(12) United States Patent
Klotz et al.

(10) Patent No.: US 10,786,544 B2
(45) Date of Patent: Sep. 29, 2020

(54) METHOD FOR TREATING CANCER

(71) Applicant: SUNNYBROOK RESEARCH INSTITUTE, Toronto (CA)

(72) Inventors: Laurence H. Klotz, Toronto (CA); Vasundara Venkateswaran, Toronto (CA)

(73) Assignee: SUNNYBROOK RESEARCH INSTITUTE, Toronto, Ontario (CA)

( * ) Notice: Subject to any disclaimer, the term of this patent is extended or adjusted under 35 U.S.C. 154(b) by 0 days.

(21) Appl. No.: 16/597,136

(22) Filed: Oct. 9, 2019

(65) Prior Publication Data

US 2020/0101131 A1 Apr. 2, 2020

Related U.S. Application Data

(63) Continuation of application No. 15/552,350, filed as application No. PCT/CA2016/050362 on Mar. 29, 2016, now Pat. No. 10,500,248.

(60) Provisional application No. 62/139,976, filed on Mar. 30, 2015.

(51) Int. Cl.
| | |
|---|---|
| A61K 38/095 | (2019.01) |
| A61K 31/337 | (2006.01) |
| A61K 45/06 | (2006.01) |
| A61P 35/04 | (2006.01) |
| A61P 35/00 | (2006.01) |

(52) U.S. Cl.
CPC .......... *A61K 38/095* (2019.01); *A61K 31/337* (2013.01); *A61K 45/06* (2013.01); *A61P 35/00* (2018.01); *A61P 35/04* (2018.01)

(58) Field of Classification Search
None
See application file for complete search history.

(56) References Cited

U.S. PATENT DOCUMENTS

| 10,500,248 B2 * | 12/2019 | Klotz ................ A61K 45/06 |
| 2014/0142168 A1 | 5/2014 | Barthomeuf |

FOREIGN PATENT DOCUMENTS

| CA | 2338073 | 2/2000 |
| CA | 2840959 | 8/2014 |
| EP | 1700598 | 9/2006 |
| JP | 2002521348 | 7/2002 |
| JP | 2009515167 | 4/2009 |
| WO | WO 2007/056012 | 5/2007 |

OTHER PUBLICATIONS

Tam and Michaud "Cabazitaxel: Just another taxane for prostate cancer?" HemOnc Today , https://www.healio.com/hematology-oncology/genitourinary-cancer/news/print/hemonc-today/%7Bde1a70ef-f0e6-4dd5-a477-c4bbde133291%7D/cabazitaxel-just-another-taxane-for-prostate-cancer (Year: 2011).*
Alonso, et al, "Antimetastatic Effect of Esmopressin in a Mouse Mammary Tumor Model," Breast Cancer Research and Treatment, Oct. 1999, vol. 57 (3), pp. 271-275.
Anomymous. "AVPR1B" https://www.proteinatlas.org/ENSG00000198049-AVPR1B/pathology, 2017.
Anonymous. "AVPR2" https://www.proteinatlas.org/ENSG00000126895-avpr2/PATHOLOGY, 2017.
Anonymous. "Expression of AVPR1A in cancer—Summary—The Human Protein Atlas", https://www.proteinatlas.org/ENSG00000166148-AVPR1A/pathology, 2017.
Bacharach, et al. "In Vivo Patterns of Expression of Urokinase and its Inhibitor PAI-1 Suggest a Concerted Role in Regulating Physiological Angiogenesis," Proceedings of the National Academy of Sciences of the United States of America, Nov. 1992, vol. 89 (22), pp. 10686-10690.
Bajou, et al., "The Plasminogen Activator Inhibitor PAI-1 Controls in Vivo Tumor Vascularization by Interaction with Proteases, Not Vitronectin. Implications for Antiangiogenic Strategies," The Journal of Cell Biology, Feb. 2001, vol. 152 (4), pp. 777-784.
Berthold, et al., "Docetaxel Plus Prednisone or Mitoxantrone Plus Prednisone for Advanced Prostate Cancer: Updated Survival in the TAX 327 Study," Journal of Clinical Oncology, Jan. 2008, vol. 26 (2), pp. 242-245.
Bologna, et al., "Bombesin Stimulates Growth of Human Prostatic Cancer Cells in Vitro," Cancer, May 1989, vol. 63 (9), pp. 1714-1720.
Canadian Patent Application No. 2,977,061, Office Action dated Jul. 6, 2018.
Chappuis, et al., "Functional Evaluation of Plasmin Formation in Primary Breast Cancer," Journal of Clinical Oncology, May 2001, vol. 19 (10), pp. 2731-2378.
Danø et al., "Plasminogen Activators, Tissue Degradation, and Cancer," Advances in Cancer Research, Jul. 1985, vol. 44, pp. 139-266.
Danø et al., "The Receptor for urokinase plasminogen activator: Stromal Cell Involvement in Extracellular Proteolysis During Cancer Invasion," Proteolysis and Protein Turnover, 1993, pp. 239-245.
European Patent Application No. 16771138.1, Extended European Search Report dated Jul. 2, 2018.
Ferrier et al., "High tPA-Expression in Primary Melanoma of the Limb Correlates with Good Prognosis," British Journal of Cancer, Nov. 2000, vol. 83 (10), pp. 1351-1359.
Festuccia et al., "Osteoblasts Modulate Secretion of Urokinase-Type Plasminogen Activator (uPA) and Matrix Metalloproteinase-9 (MMP-9) in Human Prostate Cancer Cells Promoting Migration and Matrigel Invasion." Oncology Research, Jan. 1999, vol. 11 (1), pp. 17-31.
Festuccia et al.. "Plasminogen Activator System Modulates Invasive Capacity and Proliferation in Prostatic Tumor Cells," Clinical & Experimental Metastasis, Aug. 1998, vol. 16 (6), pp. 513-528.

(Continued)

*Primary Examiner* — Larry D Riggs, II
*Assistant Examiner* — Zachary J Miknis
(74) *Attorney, Agent, or Firm* — Hueschen and Sage

(57) ABSTRACT

The present disclosure relates to a method of treating prostate cancer comprising administering to a subject in need thereof a therapeutically effective amount of a vasopressin analogue.

2 Claims, 11 Drawing Sheets

(56) References Cited

OTHER PUBLICATIONS

Forbes et al., "Increased Levels of Urokinase Plasminogen Activator Receptor in Prostate Cancer Cells Derived from Repeated Metastasis," World Journal of Urology, Apr. 2004, vol. 22 (1), pp. 67-71.
Fridman et al., "Increased Initiation and Growth of Tumor Cell Lines, Cancer Stem Cells and Biopsy Material in Mice Using Basement Membrane Matrix Protein (Cultrex or Matrigel) Co-Injection," Nature Protocols, May 2012, vol. 7 (6), pp. 1138-1144.
Friedland et al., "A phase II Trial of Docetaxel (Taxotere) in Hormone-Refractory Prostate Cancer: Correlation of Antitumor Effect Phosphorylation of Bcl-2," Seminars in oncology, Oct. 1999, vol. 26 (5 Suppl 17), pp. 19-23.
Gately et al., "The Mechanism of Cancer-Mediated Conversion of Plasminogen to the Angiogenesis Inhibitor Angiostatin," Proceedings of the National Academy of Sciences of the United States of America, Sep. 1997, vol. 94 (20), pp. 10868-10872.
Giron et al., "Desmopressin Inhibits Lung and Lymph Node Metastasis in a Mouse Mammary Carcinoma Model of Surgical Manipulation," Journal of Surgical Oncology, Sep. 2002, vol. 81 (1), pp. 38-44.
Gomez, D.E., et al., Cancer Therapy, vol. 2, p. 279-290, Sep. 2004.
Gomez, et al., "Potential application of desmopressin as a perioperative adjuvant in cancer surgery. Biological effects, antitumor properties and clinical usefulness" Cancer Therapy, 2004, 2:279-290.
Hanahan et al., "The Hallmarks of Cancer Review," Cell, Jan. 2000, vol. 100 (1), pp. 57-70.
Hildenbrand et al., "Modulators of the Urokinase-Type Plasminogen Activation System for Cancer," Expert Opinion on Investigational Drugs, May 2010, vol. 19 (5), pp. 641-652.
Husain et al., "Purification and Partial Characterization of a Single-Chain Molecular Weight of Urokinase from Human Urine," Archives of Biochemistry and Biophysics, Jan. 1983, vol. 220 (1), pp. 31-38.
Immordino et al., "Preparation, Characterization, Cytotoxicity and Pharmacokinetics of Liposomes Containing Docetaxel," Journal of Controlled Release, Sep. 2003, vol. 91 (3), pp. 417-429.
International Patent Application No. PCT/CA2016/050362, International Preliminary Report dated Jul. 18, 2017.
International Search Report for PCT/CA2016/050362 dated May 26, 2016.
Jarrard et al., "Effect of Epidermal Growth Factor on Prostate Cancer Cell Line PC3 Growth and Invasion," The Prostate, Jan. 1994, vol. 24 (1), pp. 46-53.
Jemal et al., "Cancer Statistics, 2008," CA: A Cancer Journal for Clinicians, Mar. 2008, vol. 58 (2), pp. 71-96.
Kaufmann et al., "Cellular Mechanisms of the Hemostatic Effect of Desmopressin (DDAVP)," Journal of Thrombosis and Haemostasis, Apr. 2003, vol. 1(4), pp. 682-689.
Kristensen et al., "Human Endothelial Cells Contain One Type of Plasminogen Activator," Federation of European Biochemical Societies, Mar. 1984, vol. 168 (1), pp. 33-37.
Liang et al., "In Vitro Scratch Assay: A Convenient and Inexpensive Method for Analysis of Cell Migration In Vitro." Nature Protocols, Mar. 2007, vol. 2 (2), pp. 329-333.
Mackler et al., "Drug Insight : Use of Docetaxel in Prostate and Urothelial Cancers," Nature Clinical Practice Urology, Feb. 2005, vol. 2 (2), pp. 92-100.
Mannucci et al., "Mechanism of Plasminogen Activator and Factor VIII Increase after Vasoactive Drugs," British Journal Haematology, May 1975, vol. 30 (1), pp. 81-93.
Mannucci, "Desmopressin (DDAVP) in the Treament of Bleeding Disorders: The First Twenty Years," Blood, Oct. 1997, vol. 90 (7), pp. 2515-2521.
Matuo et al., "Thrombosis by Human Tissue Plasminogen Activator and Urokinase in Rabbits with Experimental Pulmonary Embolus," Nature, Jun. 1981, vol. 291, pp. 590-591.
Merchan et al., "In Vitro and in Vivo Induction of Antiangiogenic Activity by Plasminogen Activators and Captopril," Journal of the National Cancer Institute, Mar. 2003, vol. 95 (5), pp. 388-399.
Morgan et al., "Human Breast Cancer Cell-Mediated Bone Collagen Degradation Requires Plasminogen Activation and Matrix Metalloproteinase Activty," International Federation for Cell Biology, Feb. 2005, vol. 5 (1), 1 page.
North et al., "MCF-7 Breast Cancer Cells Express Normal Forms of All Vasopressin Receptors Plus an Abnormal V2R," Peptides, Aug. 1999, vol. 20 (7), pp. 837-842.
North, "Gene Regulation of Vasopressin and Vasopressin Receptors in Cancer," Experimental Physiology, Mar. 2000, vol. 85, pp. 27S-40S.
Peacock, S., "Exploitation of androgen receptor signaling by guanine nucleotide exchange factor Vav3 in castration resistant prostate cancer", Dissertation, University of Miami, 2013.
Petylak et al., "Docetaxel and Estramustine Compared with Mitoxantron and Prednisone for Advanced Refractory Prostate Cancer," The New England Journal of Medicine, Oct. 2004, vol. 351 (15), pp. 1513-1520.
Picus et al., "Docetaxel (Taxotere) as Monotherapy in the Treatment Hormone-Refractory Prostate Cancer: Preliminary Results," Seminars in Oncology, Oct. 1999, vol. 26 (5 Suppl 17), pp. 14-18.
Pienta, "Preclinical Mechanisms of Action of Docetaxel and Docetaxel Combinations in Prostate Cancer," Seminars in Oncology, Aug. 2001, vol. 28 (4 Suppl 15), pp. 3-7.
Quax et al., "Plasminogen Activator and Matrix Metalloproteinase Production and Extracellular Matrix Degradation by Rat Prostate Cancer Cells in Vitro: Correlation with Metastatic Behavior in Vivo," The Prostate, Aug. 1997, vol. 32 (3), pp. 196-204.
Rabbani, "Metalloproteases and Urokinase in Angiogenesis and Tumor Progression," In vivo (Athens, Greece), Jan. 1998, vol. 12 (1), pp. 135-142.
Rezakhaniha, B., et al., J. Res. Med. Sci., vol. 16, No. 4, p. 516-523, Apr. 2011.
Richardson et al., "Desmopressin," Annals of Internal Medicine, Aug. 1985, vol. 103 (2), pp. 228-239.
Ripoll et al., "Antitumor Effects of Desmopressin in Combination with Chemotherapeutic Agents in a Mouse Model of Breast Cancer," Anticancer Research, Jun. 2008, vol. 28 (5A), pp. 2607-2612.
Ripoll et al., "Effects of the Synthetic Vasopressin Analog Desmopressin in a Mouse Model of Colon Cancer," Anticancer Research, Dec. 2010, vol. 30 (12), pp. 5049-5054.
Ripoll et al., "Reduction of Tumor Angiogeneis induced by Desmopressin in a Breast Cancer Model," Breast Cancer Research and Treatment, Nov. 2013, vol. 142 (1), pp. 9-18.
Sasaki, et al., "A combination of desmopressin and docetaxel inhibit cell proliferation and invasion mediated by urokinase-type plasminogen activator (uPA) in human prostate cancer cells", Biochem. & Biophys. Res. Comm., 464, 2015, pp. 848-854.
Sasaki, H., et al., Biochem. Biophy. Res. Commun. vol. 464, p. 848-854, Jul. 13, 2015.
Tannock et al., "Docetaxel Plus Prednisone or Mitoxantrone Plus Prednisone for Advanced Prostate Cancer," The New England Journal Medicine, Oct. 2004, vol. 351 (15), pp. 1502-1512.
Terraube et al., "Increased Metastatic Potential of Tumor Cells in Von Willebrand Factor-Deficient Mice," Journal of Thrombosis and Haemostasis, Mar. 2006, vol. 4 (3), pp. 519-526.
Terraube et al., "Role of Von Willebrand Factor in Tumor Metastasis," Thrombosis Research, Oct. 2007, vol. 120 (Suppl 2), pp. S64-S70.
Venier et al., "Capsaicin: A Novel Radio-Sensitizing Agent for Prostate Cancer," The Prostate, Feb. 2015, vol. 75 (2), pp. 113-125.
Venkateswaran et al., "Selenium Modulation of Cell Proliferation and Cell Cycle Biomarkers in Human Prostate Carcinoma Cell Lines Selenium Modulation of Cell Proliferation and Cell Cycle Biomarkers in Human Prostate Carcinoma Cell Lines," Cancer Research, May 2002, vol. 62 (9), pp. 2540-2545.
Written Opinion for Application No. PCT/CA2016/50362, dated Jun. 13, 2016, 7 pages.
Yamazaki, et al., "Prostate adenocarcinoma producing syndrome of inappropriate secretion of antidiuretic hormone", Intl. J. Urology 8, 2001, pp. 513-516.

(56) References Cited

OTHER PUBLICATIONS

Zhong et al., "Oxytocin Induces the Migration of Prostate Cancer Cells: Involvement of the Gi-Coupled Signaling Pathway." Molecular Cancer Research, Aug. 2010, vol. 8 (8), pp. 1164-1172.
Gomez, et al., "Desmopressin and Other Synthetic Vasopressin Analogues in Cancer Treatment" Bulletin du Cancer, Feb. 2006, vol. 93(2), pp. E7-E12.
Japanese Patent Application No. 2017-551315, Office Action dated Jan. 6, 2020.
U.S. Appl. No. 15/552,350, Final Office Action dated Jun. 24, 2019.
U.S. Appl. No. 15/552,350, Non-Final Office Action dated Oct. 18, 2018.
U.S. Appl. No. 15/552,350, Notice of Allowance dated Aug. 22, 2019.
U.S. Appl. No. 15/552,350, Notice of Allowance dated Oct. 25, 2019.
U.S. Appl. No. 15/552,350, Restriction Requirement dated Jul. 3, 2018.
Gomez, et al., Bull Cancer, 2006, 93(2), E7-E12.
European Patent Application No. 16771138.1, Communication pursuant to Article 94(3) EPC dated Apr. 6, 2020.

\* cited by examiner

FIG. 1A
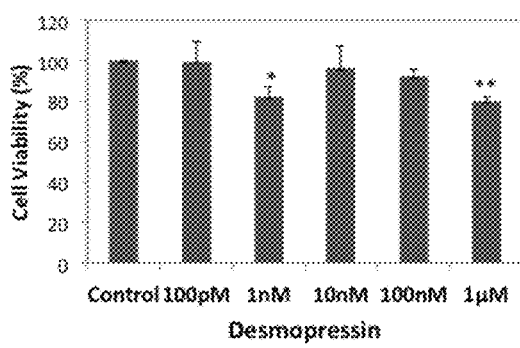
FIG. 1B
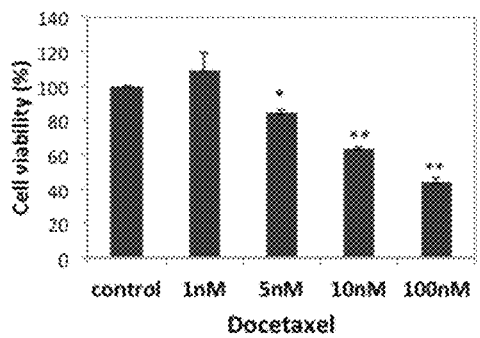
FIG. 1C
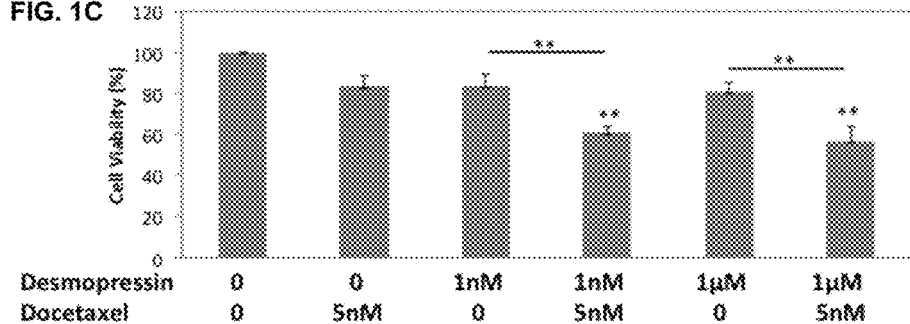
FIG. 2A
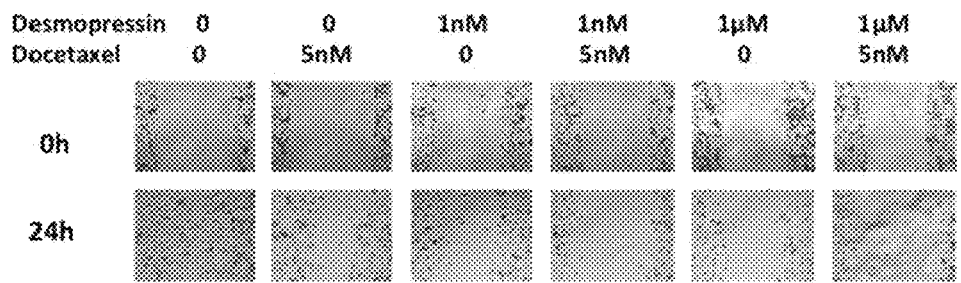
FIG. 2B
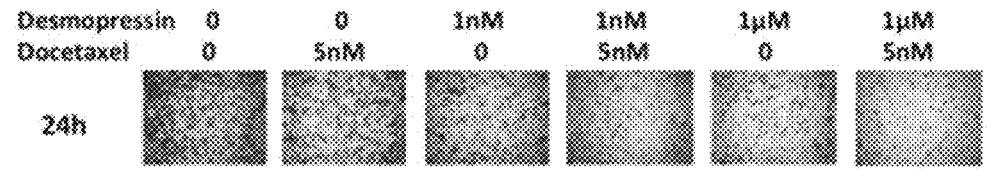
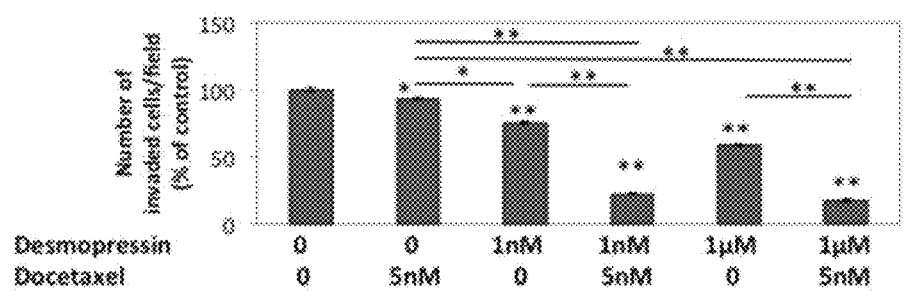
FIG. 2C \* $p<0.05$ for combination on 100nM DTX and 1μM Desmopressin
\*\* $p<0.05$ for 10nM and 100nM DTX or combined with 1μM Desmopressin compared to control (0.01% DMSO solution in media).

* $P<0.05$
** wound closure for treatments involving 100nM DTX are presented, but could only be estimated and not analysed for significance.

Wound healing representative pictures

Time Zero        24 hours

Cells only (control)

DTX 10μM

Desmopressin only

DTX + Desmopressin

* P < 0.05 for combined therapy compered to DTX only

Animal weight measurement during treatment period

Measurements were done twice a week starting at treatment day #1.
No statistical significant difference in animal weight was noted during treatment period

Representative pictures of mice and tumors
Mice representative pictures
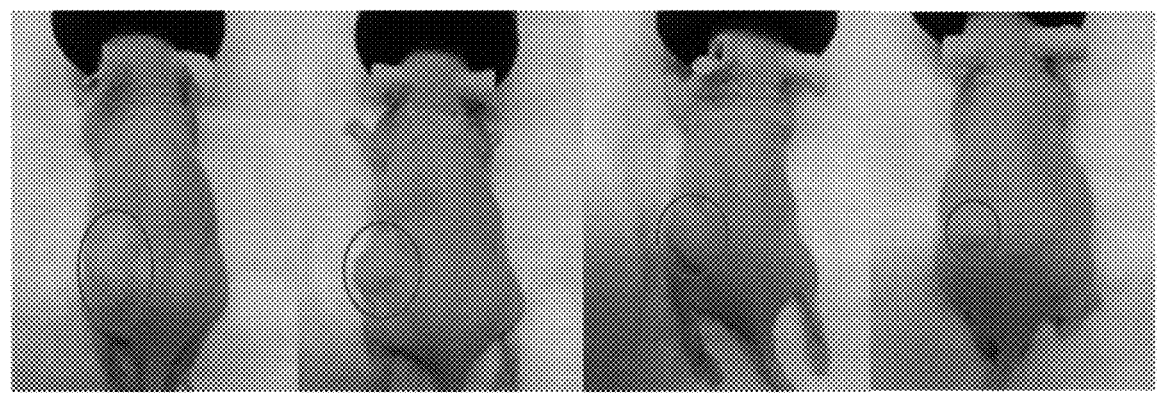
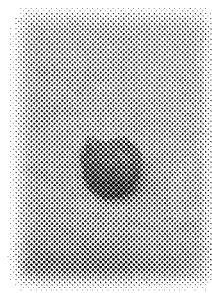
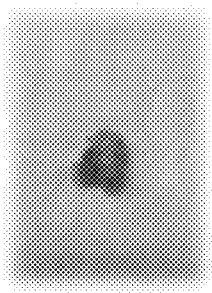
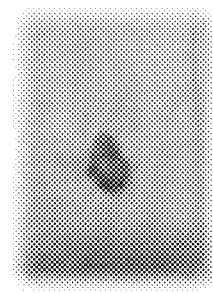
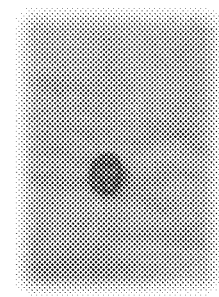
| control | Desmopressin only | Docetaxel only | Docetaxel + Desmopressin |
|---|---|---|---|
| FIG. 15A | FIG. 15B | FIG. 15C | FIG. 15D |

METHOD FOR TREATING CANCER

RELATED APPLICATIONS

This Application claims priority to U.S. 62/139,976, filed Mar. 30, 2015, the entire contents of which is hereby incorporated by reference.

FIELD

The present disclosure relates to a method of treating cancer using a vasopressin analogue. In particular, the disclosure relates to a method of treating prostate cancer comprising administering a vasopressin analogue.

INTRODUCTION

Prostate cancer is the second leading cause of cancer-related deaths in Western countries.[1] Most patients dying of prostate cancer have metastatic castrate resistant disease (CRPC).[2] There is no curative agent for treatment of CRPC.

Docetaxel is first drug of choice for management of CRPC.[3,4] Although Docetaxel-based combination chemotherapy has significantly improved survival of CRPC patients, durable responses are uncommon.[4-6] Furthermore, Docetaxel causes adverse events such as grade 3 or 4 neutropenia, fatigue, alopecia and nausea. High dose docetaxel induces significant toxicity.[4,5,7]

Desmopressin is a synthetic derivative of antidiuretic hormone.

Desmopressin is a safe and effective hemostatic agent in patients with von Willbrand disease, hemophilia A and other bleeding disorders.[8-10] Desmopressin induces an increase in the plasma level of coagulation factor VIII, von Willbrand factor (VWF) and tissue plasminogen activator (t-PA).[9] Recent reports suggest that desmopressin inhibits tumor metastasis in in vivo models.[11-13] Alonso et al. reported that desmopressin inhibits lung colonization by blood-borne breast cancer cells in an in vivo model.[11] Desmopressin injected preoperatively reduced lymph node and lung metastasis in a mammary tumor model.[12] Desmopressin impairs aggressiveness of residual mammary tumors during chemotherapy.[13]

SUMMARY

The present disclosure relates to a method of treating cancer using a vasopressin analogue, such as desmopressin. In particular, the method relates to the treatment of prostate cancer.

In one embodiment, the disclosure includes a method of treating prostate cancer comprising administering to a patient in need thereof a therapeutically effective amount of desmopressin or a vasopressin analogue thereof.

In one embodiment, the method further comprises co-administering to a patient in need thereof a pharmaceutical composition a taxane or a functional derivative thereof.

In one embodiment, the disclosure relates to a method of treating metastatic castrate-resistant prostate cancer, comprising administering to a subject in need thereof, a therapeutically effective amount of vasopressin analogue, such as desmopressin.

In another embodiment of the disclosure, there is also included a use of a therapeutically effective amount of a vasopressin analogue, such as desmopressin, for the treatment of prostate cancer. In one embodiment, the disclosure includes a use of a therapeutically effective amount of (i) desmopressin or a vasopressin analogue thereof; and (ii) a taxane or a functional derivative thereof, for the treatment of prostate cancer.

In another embodiment of the disclosure, there is also included a use of a therapeutically effective amount of a vasopressin analogue, such as desmopressin, for the treatment of metastatic castrate-resistant prostate cancer.

The disclosure also includes kit for the treatment of prostate cancer, comprising (i) a therapeutically effective amount of a vasopressin analogue, such as desmopressin, and (ii) a therapeutically effect amount of a taxane or a functional derivative thereof, and instructions for using the kit.

Other features and advantages of the present application will become apparent from the following detailed description. It should be understood, however, that the detailed description and the specific examples while indicating preferred embodiments of the application are given by way of illustration only, since various changes and modifications within the spirit and scope of the application will become apparent to those skilled in the art from this detailed description.

DRAWINGS

The disclosure will now be described in greater detail with reference to the following drawings in which FIG. 1A is a bar graph showing the effects of desmopressin on PC3 cells; FIG. 1B is a bar graph showing the effects of docetaxel on PC3 cells; FIG. 1C is a bar graph showing the effects of docetaxel and desmopressin, alone or in combination, on PC3 cells;

FIG. 2A are micrographs showing the effect of docetaxel and desmopressin, alone or in combination, on cell migration; FIG. 2B are micrographs showing the effect of docetaxel and desmopressin, alone or in combination, on cell invastion; FIG. 2C is a bar graph showing the effect of docetaxel and desmopressin, alone or in combination, on cell migration;

Figure 13:
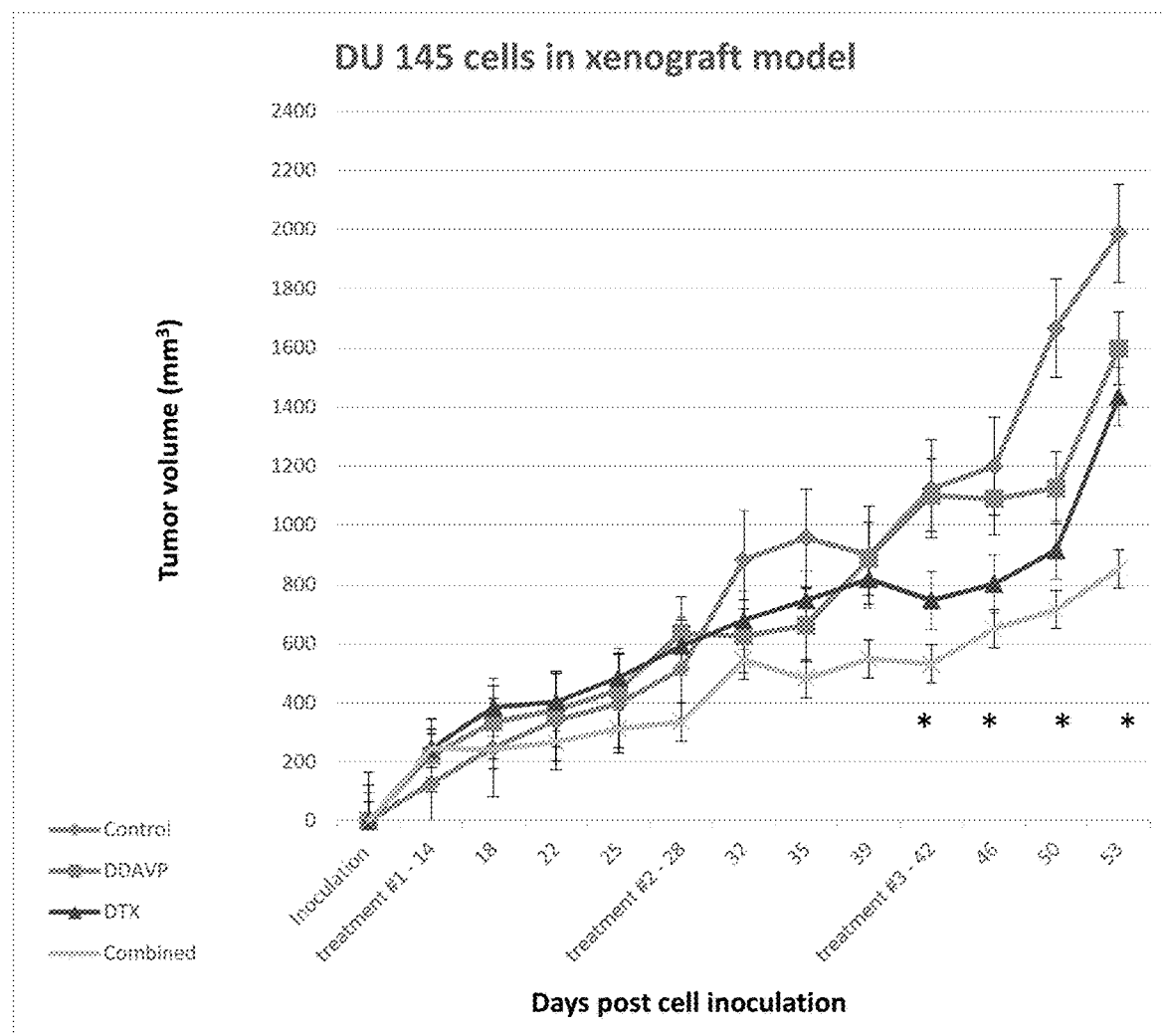
Figure 14:
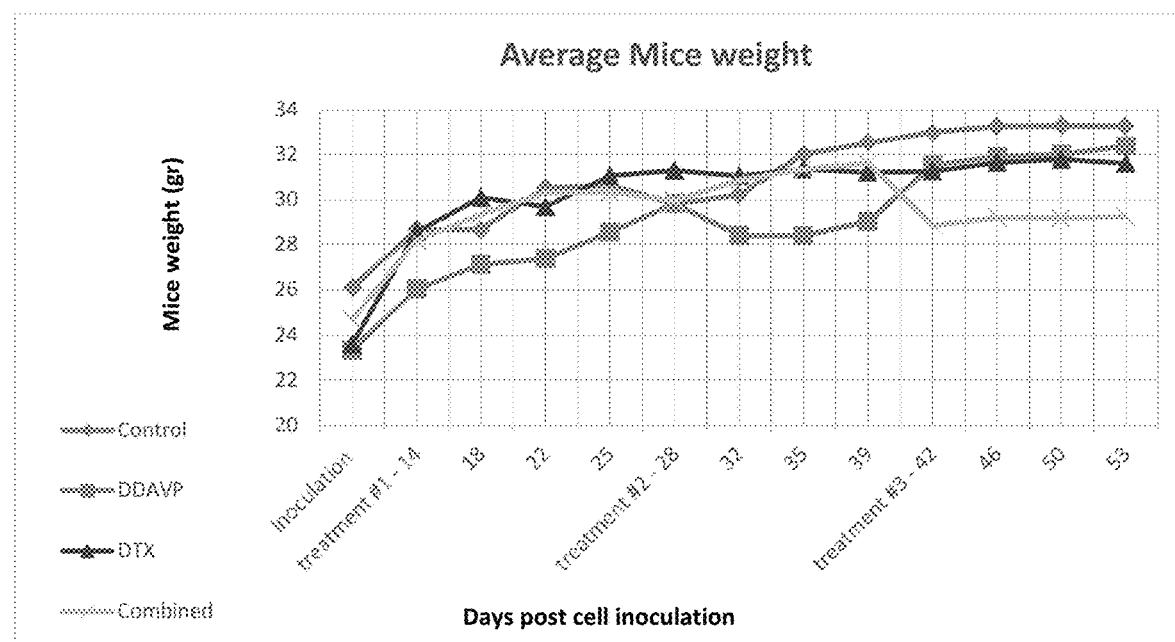

FIG. 12A-D are micrographs showing the effects of docetaxel (DTX) or desmopressin (Desmo), alone and/or in combination, on DU145 cells, assessed using wound healing assay;

FIG. 13 is a graph depicting the effects of docetaxel and desmopressin, alone and/or in combination, on tumor volume in a prostate cancer xenograft model;

FIG. 14 is a graph depicting the effects of docetaxel and desmopressin, alone and/or in combination, on body weight of animals in a prostate cancer xenograft model;

FIG. 15A-D are micrographs showing the effects of docetaxel and desmopressin, alone and/or in combination, on tumor size in a prostate cancer xenograft model.

DESCRIPTION OF VARIOUS EMBODIMENTS (I) Definitions

The term "vasopressin analogue" as used herein, refers to compounds or derivatives having similar function to vasopressin but not necessarily a similar structure, and includes all compounds or derivatives having anti-proliferative activity, including prodrugs. Vasopressin analogues include, but are not limited to, synthetic arginine vasopressin, lysine vasopressin, terlipressin, felypressin, or ornipressin. As used herein, the term "desmopressin" or "DDAVP®", a vasopressin analogue, refers to 1-desamino-8-D-arginine vasopressin.

As used herein, the term "taxane" generally refers to a class of diterpenes produced and isolated from natural sources such as the plants of the genus *Taxus* (Yew tree), or from cell culture. This term also includes those taxanes that have been artificially synthesized. For example, this term includes docetaxel and paclitaxel, and derivatives thereof. Also included are "functional derivatives" of taxanes also having anti-proliferative activity, including prodrugs.

The term "pharmaceutically acceptable" as used herein means compatible with the treatment of subjects, for example, humans.

The term "pharmaceutically acceptable salt" refers, for example, to a salt that retains the desired biological activity of a compound of the present disclosure and does not impart undesired toxicological effects thereto; and may refer to an acid addition salt or a base addition salt.

As used herein, the phrase "castrate resistant prostate cancer" (also known as hormone-refractory prostate cancer or androgen-independent prostate cancer or endocrine resistant prostate cancer) refers to prostate cancer which is resistant to hormone therapy.

As used herein, the term "metastatic" is defined as the transfer of cancer cells from one organ or part to another not directly connected with it.

As used herein, a "subject" refers to all members of the animal kingdom including mammals, and suitably refers to humans. A member of the animal kingdom includes, without limitation, a mammal (such as a human, primate, swine, sheep, cow, equine, horse, camel, canine, dog, feline, cat, tiger, leopard, house pet, livestock, rabbit, mouse, rat, guinea pig or other rodent, seal, whale and the like). In an embodiment of the present disclosure, the subject is in need of a treatment of the disclosure.

As used herein, the term "prodrug" refers to a substance that is prepared in an inactive form that is converted to an active form (i.e., drug) within the body or cells thereof by the action of, for example, endogenous enzymes or other chemicals and/or conditions. Prodrug derivatives of desmopressin, or pharmaceutically acceptable salts or solvates thereof, can be prepared by methods known to those of ordinary skill in the art.

The term "therapeutically effective amount" as used herein means an amount effective, at dosages and for periods of time necessary to achieve the desired result. Effective amounts may vary according to factors such as the disease state, age, sex and/or weight of the subject. The amount of a given compound or composition that will correspond to such an amount will vary depending upon various factors, such as the given drug or compound, the pharmaceutical formulation, the route of administration, the identity of the subject being treated, and the like, but can nevertheless be routinely determined by one skilled in the art.

The term "administered" or "administering" as used herein means administration of a therapeutically effective dose of a compound or composition of the disclosure to a subject.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

(II) Method for the Treatment of Cancer

The present disclosure relates to the treatment of cancer. In particular, the present disclosure relates to the treatment of prostate cancer, comprising administering to a patient in need thereof a therapeutically effective amount of a vasopressin analogue. In other embodiments, the disclosure includes a method for the treatment of hormone dependent cancers, such as lung, uterine, kidney, ovarian, testicular, breast or colorectal comprising administering to a patient in need thereof a therapeutically effective amount of a vasopressin analogue.

In one embodiment, the present disclosure relates to a method of treating prostate cancer comprising administering to a patient in need thereof a therapeutically effective amount of a vasopressin analogue. In one embodiment, the vasopressin analogue is desmopressin, synthetic arginine vasopressin, lysine vasopressin, terlipressin, felypressin, or ornipressin. In a further embodiment, the vasopressin analogue is desmopressin.

In another embodiment of the disclosure, there is also included a use of a therapeutically effective amount of a vasopressin analogue, for the treatment of prostate cancer. In another embodiment of the disclosure, there is also included a use of a therapeutically effective amount of a vasopressin analogue, for the manufacture of a medicament for the treatment of prostate cancer. In one embodiment, the vasopressin analogue is desmopressin. In other embodiments, the disclosure includes a use of a therapeutically effective amount of a vasopressin analogue, for the treatment of hormone dependent cancers, such as lung, uterine, kidney, ovarian, testicular, breast or colorectal.

In one embodiment, the prostate cancer is metastatic prostate cancer. In another embodiment, the prostate cancer is castrate-resistance prostate cancer. In a further embodiment, the cancer is metastatic castrate-resistant prostate cancer.

In another embodiment of the disclosure, desmopressin or an analogue thereof is administered to the subject, for example, a prodrug of desmopressin. Prodrugs of desmopressin include aliphatic carboxylic acid esters and carbonate esters of the tyrosine phenolic group. In another embodiment, desmopressin is administered to the subject.

In another embodiment of the disclosure, the method further comprises co-administering a taxane. As used herein, the term "co-administer," is intended to embrace separate administration of the vasopressin analogue, such as desmopressin, and the taxane (or functional derivative) in a sequential manner as well as co-administration of these agents in a substantially simultaneous manner, such as in a single mixture/composition or in doses given separately, but nonetheless administered substantially simultaneously to the subject.

In one embodiment, the taxane is docetaxel, paclitaxel, larotaxel, cabazitaxel, baccatin, cephalomannine, brevifoliol, BMS-275183, abraxane, taxoprexin, xytotax or functional derivatives thereof. In another embodiment, the taxane is docetaxel, paclitaxel, cabazitaxel or functional derivatives thereof. In a further embodiment, the taxane is docetaxel.

In an embodiment of the disclosure, the vasopressin analogue is administered at a dose effective to reduce or halt proliferation of the cancer cells, for example by inducing cell cycle arrest. In one embodiment, the cancer cells are prostate cancer cells. In another embodiment, the vasopressin analogue is desmopressin.

In another embodiment of the disclosure, the vasopressin analogue is administered at a dose effective to reduce or halt cancerous tumour growth, and decrease tumour volume. In one embodiment, the cancerous tumour growth is a cancerous prostate tumour. In one embodiment, the vasopressin analogue is desmopressin.

In another embodiment of the disclosure, the vasopressin analogue is administered at a dose effect to reduce or prevent metastases of cancer cells to other tissues and organs of the subject's body. In one embodiment, the cancer cells are prostate cancer cells. In one embodiment, the vasopressin analogue is desmopressin.

In another embodiment of the disclosure, the vasopressin analogue is co-administered with a taxane or functional derivative thereof, at a dose which enhances the antiproliferative efficacy of the taxane. In one embodiment, the vasopressin analogue is desmopressin. It is well known to those skilled in the art that taxanes cause serious side-effects such as grade 3 or 4 neutropenia. The administration of a vasopressin analogue, such as desmopressin, thereof allows for the use of less toxic doses of the taxane without compromising efficacy of the taxane for the treatment of cancer.

In another embodiment of the disclosure, there is included a kit for the treatment of cancer. In one embodiment, the cancer is prostate cancer.

In one embodiment, the disclosure includes a kit for the treatment of cancer, comprising (i) a therapeutically effective amount of a vasopressin analogue, and (ii) a therapeutically effect amount of a taxane or a functional derivative thereof; and instructions for using the kit. In one embodiment, the vasopressin analogue is desmopressin.

In one embodiment, the kit is for the treatment of prostate cancer, lung, uterine, kidney, ovarian, testicular, breast or colorectal. In one embodiment, the cancer is prostate cancer. In another embodiment, the prostate cancer is metastatic prostate cancer. In another embodiment, the kit is for the treatment of castrate-resistance prostate cancer. In a further embodiment, the kit is for the treatment of metastatic castrate-resistant prostate cancer.

In another embodiment of the disclosure, the kit comprises a vasopressin analogue which is administered to the subject. In another embodiment, the kit comprises desmopressin which is administered to the subject.

In another embodiment of the disclosure, the kit comprises a taxane which is co-administered (with the vasopressin analogue) to the subject. Co-administration encompasses separate administration of the vasopressin analogue (such as desmopressin) and the taxane (or functional derivative) in a sequential manner as well as co-administration of these agents in a substantially simultaneous manner, such as in a single mixture/composition or in doses given separately, but nonetheless administered substantially simultaneously to the subject.

In one embodiment, the kit comprises a taxane which is docetaxel, paclitaxel, larotaxel, cabazitaxel, baccatin, cephalomannine, brevifoliol, BMS-275183, abraxane, taxoprexin or xytotax, or functional derivatives thereof. In another embodiment, the taxane is docetaxel, paclitaxel, cabazitaxel or functional derivatives thereof. In a further embodiment, the taxane is docetaxel.

In one embodiment, the vasopressin analogue, such as desmopressin, is formulated as a pharmaceutically acceptable salt, such as desmopressin acetate. In a further embodiment, the vasopressin analogue is formulated in a pharmaceutical composition, comprising the vasopressin analogue and a pharmaceutically acceptable excipient and/or carrier. In one embodiment, the vasopressin analogue is desmopressin.

In one embodiment, the vasopressin analogue, for example desmopressin acetate, is formulated as an aqueous solution of desmopressin acetate present at a concentration of about 4 µg/ml or about 15 µg/ml. In one embodiment, the vasopressin analogue is administered at a dose of between about 0.1 µg/kg to about 1.0 µg/kg, optionally 0.2 µg/kg to about 0.5 µg/kg or about 0.4 µg/kg. In one embodiment, the vasopressin analogue is formulated for intravenous, intramuscular or subcutaneous administration. In one embodiment, the vasopressin analogue is formulated for immediate release, IV infusion, delayed release or depot administration.

In one embodiment, the taxane or functional derivative thereof is formulated in a pharmaceutical composition, comprising the taxane and a pharmaceutically acceptable excipient and/or carrier.

In one embodiment, the taxane is docetaxel. In a further embodiment, the docetaxel is formulated in an aqueous solution present at a concentration of between about 50 mg/ml to about 100 mg/ml, optionally about 80 mg/ml. In one embodiment, the docetaxel is administered at a dose between about 50 mg/m2 to about 100 mg/m2, or about 75 mg/m2, every 3 weeks as a 1 hour intravenous infusion. Optionally, prednisone 5 mg orally twice daily is administered concurrently with the docetaxel. In one embodiment, the docetaxel is formulated for intravenous administration.

The pharmaceutical forms suitable for injectable use include sterile aqueous solutions or dispersion and sterile powders for the extemporaneous preparation of sterile injectable solutions or dispersions. In all cases the form must be sterile and must be fluid to the extent that easy syringability exists.

In one embodiment, the taxane is administered to the patient every three weeks for four cycles, and the vasopressin analogue is administered about 30 minutes before the dose of taxane is administered, and also 24 hours after the dose of taxane is administered.

Although the disclosure has been described in conjunction with specific embodiments thereof, if is evident that many alternatives, modifications and variations will be apparent to those skilled in the art. Accordingly, it is intended to embrace all such alternatives, modifications and variations that fall within the spirit and broad scope of the appended claims. In addition, citation or identification of any reference in this application shall not be construed as an admission that such reference is available as prior art to the present disclosure.

The operation of the disclosure is illustrated by the following representative examples. As is apparent to those skilled in the art, many of the details of the examples may be changed while still practicing the disclosure described herein.

(III) Examples

The operation of the disclosure is illustrated by the following representative examples. As is apparent to those skilled in the art, many of the details of the examples may be changed while still practicing the disclosure described herein.

Example I

Materials and Methods

Cell Culture

PC3 human prostate carcinoma cells were obtained from the American Type Culture Collection (Rockville, Md., USA). Cells were cultured in DMEM/F12 medium (Invitrogen, ON, Canada) with 10% fetal bovine serum (FBS; Gibco, NY, USA), 100 IU/ml penicillin, 100 µg/ml streptomycin and 0.3 mg/ml 1-glutamine, and maintained at 37° C. in a humidified atmosphere of 5% $CO_2$ in air. Cells were grown to 80% confluence in 10-cm tissue culture plates.

Chemicals

Docetaxel was purchased from Santa Cruz Biotechnology (CA, USA). Docetaxel were prepared in dimethyl sulfoxide (DMSO; Sigma, St Louis, USA) and diluted with cell culture medium at a final concentration of 0.01% DMSO. Desmopressin was kindly provided to us by Ferring Pharmaceutical (CA, USA).

Cell Proliferation Assay

Cell proliferation was determined by MTS assay as previously described.[14] Cells ($5 \times 10^3$/well) were plated using 96 well plates. After cultivation for 24 h, a range of concentration of desmopressin (100 pM-1 µM) and/or Docetaxel (1 nM-100 nM) were added and culture continued for up to 72 h. Cell viability was assessed by incubation with MTS for 2 hours and resulting absorbance measured at 595 nm using an ELISA plate reader. In the combination studies, varying dose of each agents were tested. The experiments were repeated 3 times in triplicates and statistical analysis performed.

Wound Healing Assay

Cell motility was assessed using a wound healing assay performed according to a protocol described by Liang et al.[15]. Cells ($2 \times 10^4$/well) were plated in 6-well plate. Cells at over 90% confluence were incubated for 1 hr with 1 mg/I of mitomycin C (Sigma-Aldrich, St Louis, USA) in order to exclude proliferative effect. After mitomycin C treatment, the injury line was made using a 200 µl tip, and the cell monolayers were rinsed with PBS. The cells were treated with desmopressin and/or docetaxel and allowed to migrate for 24 h. A computer-based microscopy imaging system was used to determine wound healing after scratching the plate with a microscope at 200× magnification. Several wound areas were observed for cell migration. The experiments were repeated 3 times in triplicates.

Cell Migration and Invasion Assay

The migration of cells was measured using transwell insert plates (BD Biosciences, Bedford Mass.) according to the manufacture's protocol. Cells were subjected to 24 h of serum deprivation in DMEM/F12 supplemented with FBS. PC3 ($5 \times 10^4$) cells were plated onto filters in 8.0-µm transwell insert plates and treated with these compounds, desmopressin (1 nM, 1 µM) and 5 nM docetaxel, in serum-free medium. The lower chamber also contained 10% FBS. Cells were allowed to migrate for 24 h. After the treatment, cells remaining on the top surfaces of the filter were removed using cotton swabs. The migrated cells that are attached to the lower surface of the filter were fixed in 4% formaldehyde at room temperature for 30 min, and then stained with crystal violet for 20 min. The migrated cells from random fields were chosen and counted using the computer-based microscopy imaging system. For the invasion assay, the same procedures were performed as described in the migration assay, except that the cells were plated onto 24-well matrigel-coated transwell plates (BD Biosciences, Bedford Mass.). The experiments were repeated 2 times in duplicates and statistical analysis performed.

Flow Cytometry

To analyze cell cycle profiles, cells were plated at a density of $1 \times 10^6$ per 10 cm dish. Asynchronously growing cells were pulse labeled with 10 mM bromodeoxyuridine (BrdU) for 2 h with or without prior treatment of the antioxidants at the end of 24 h. Cells were then harvested, fixed with 70% ethanol, treated with 0.1% HCl and heated for 10 min at 90° C. to expose the labeled DNA. Cells were stained with anti-BrdU-conjugated FITC (Becton-Dickinson) and counterstained with propidium iodide, and then allowed to incubate for 30 mins on ice. Samples were filtered through a nylon mesh. Cell cycle analysis was carried out on the FACS Calibur flow cytometer using the Cell Quest Pro software package (Becton-Dickinson, CA, USA). The experiments were repeated 3 times in triplicates and statistical analysis performed as mentioned below.

Western Blot Analysis

Protein lysates from the desmopressin monotherapy dose response study (100 pM-1 uM), desmopressin monotherapy time point study (1 uM, 0-48 h) and combination study and concentrated media employed for Western blot analysis, were prepared as previously described.[14] The proteins were subjected to 10-12% SDS-PAGE and electrophoretically transferred onto a PVDF membrane at 100V/300 mA overnight using a semidry transfer apparatus (Bio-Rad Laboratories, Hercules, Calif.). After activation in methanol (100%), blots were incubated for 60 mins at room temperature in TBST containing 5% skimmed milk. After washing, the membranes were incubated with primary antibodies against Bax, bcl-2, p21 (waf1/cip1), p27 (kip1), cdk2, cdk4, uPA, uPAR, MMP-2 and MMP-9 (1:100-200, Santacruz Biotechnology, Santacruz, Calif., USA). After incubation with respective primary antibody, the membrane was washed with TBST 3 times for 5 min, then incubated with appropriate secondary antibody for 1 h at room temperature and washed with TBST 3 times for 5 min. Protein detection was performed with enhanced chemiluminescence Western blotting regents (Amersham Pharmacia Biotech, Buckinghamshire, UK).

In Vitro Studies using Xenograft

The mice were housed and maintained in laminar flow cabinets under specific pathogen-free conditions in facilities approved by the University of Toronto Animal Research Ethics Board and in accordance with their regulations and standards by the Canadian Council on Animal Care (CCAC). Cells ($1 \times 10^6$ PC3 cells with 100 µl martrigel solution (BD Biosciences, CA, USA)) were inoculated subcutaneously (sc) into 6-8 week-old male nude mice (Harlan Sprague Dawley, Inc.). After 14 days, the developing tumors were measured and mice randomly assigned to different treatment groups. Tumor volumes were determined by measurement of tumor length (L) and width (W) with a caliper and calculated according to the formula: $V=(L \times W^2)(\pi/6)$ twice a week. A tumor volume in the range of 100 mm$^3$ was required for a given mouse to be included. Using the xenograft model, tumor growth was determined for the control and each treatment mice. Mice were randomized into four groups; control (n=15), desmopressin alone (n=15), docetaxel alone (n=10) and desmopressin in combination with docetaxel (n=10). Control animals received only the saline vehicle. Desmopressin from Ferring Pharmaceuticals (Ferring Inc, CA, USA) was administrated in 2 doses, 0 h and 24 h. Mice received desmopressin intravenously in the saline at a final dose of 2 µg/ml/body weight (50 ng/0.3 ml saline dose). Mice were administrated docetaxel at a dose of 5 mg/kg intravenously as 3 weekly cycles. Desmopressin was administrated in 2 doses, 30 min prior to and 24 h after the administration of docetaxel. The animals that were administrated docetaxel or desmopressin in combination with docetaxel were sacrificed 35 days after cell inoculation. Control and desmopressin mice were monitored until tumor volume was approximately 1500 mm3 or day 49, whichever earlier, in order to evaluate antitumor effect of desmopressin in vivo study.

Statistical Analyses

All experiments were performed in triplicates. The date represented mean±the standard error of the mean. Statistical analysis was done by Student's t test at a significance level of P<0.05. Analyses of the in vivo results were performed using either Student's t-testing or repeated measures one-way ANOVA techniques.

Example 1—Effect of Docetaxel and/or Desmopressin on Cell Proliferation of PC3 Cells Docetaxel and/or desmopressin inhibit cell proliferation on PC3 cells. The MTS cell proliferation assay was conducted to investigate whether docetaxel and/or desmopressin suppresses cell proliferation. The assay was carried out at 72 h with the cells treated with a dose range of 0-100 nM docetaxel. Cell growth was expressed as a relative value to that of the untreated control cells. PC3 cells treated with docetaxel for 72 h decreased cell viability in a dose dependent manner (FIG. 1A). Cells treated with a range of doses of desmopressin (1 nM-1 µM) significantly reduced cell proliferation compared to controls by 72 h (FIG. 1B, p<0.01). Moreover, combination therapy of desmopressin (1 nM, 1 µM) and 5 nM docetaxel also resulted in a significant decrease in cell proliferation (FIG. 1C, p<0.01).

Example 2—Differential Influences of Desmopressin on Migration of PC3 Cells in a Dose Dependent Manner Since desmopressin and docetaxel treatment resulted in anti-proliferative effect on PC3 cells in culture, the effect of desmopressin alone (1 nM, 1 µM) and in combination with 5 nM docetaxel treatment on cell migration by the wound-healing assay was determined. As shown in FIG. 2, the difference in distance migrated by control between 0 h and 24 h was measured and compared with that of the treated cells. At the end of 24 h, a significant decrease in cell migration with a combination of desmopressin and docetaxel was observed (FIG. 2A). The migratory capacity of cells was further quantified using the migration chamber transwell plates. Different doses of desmopressin (1 nM and 1 µM) treatment significantly inhibited cell migration (FIGS. 2B and C, p<0.01). Moreover, each combination treatment with desmopressin (1 nM and 1 µM) and 5 nM docetaxel resulted in a further significant reduction in cell migration (FIGS. 2B and C, p<0.01).

Example 3—Anti-Invasive Effects of Desmopressin on PC3 Cells

Figure 3A:
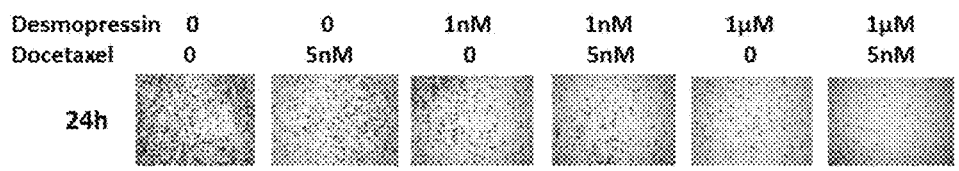
FIG. 3A are micrographs showing the anti-invasive effects of docetaxel and desmopressin, alone or in combination.
Figure 3B:
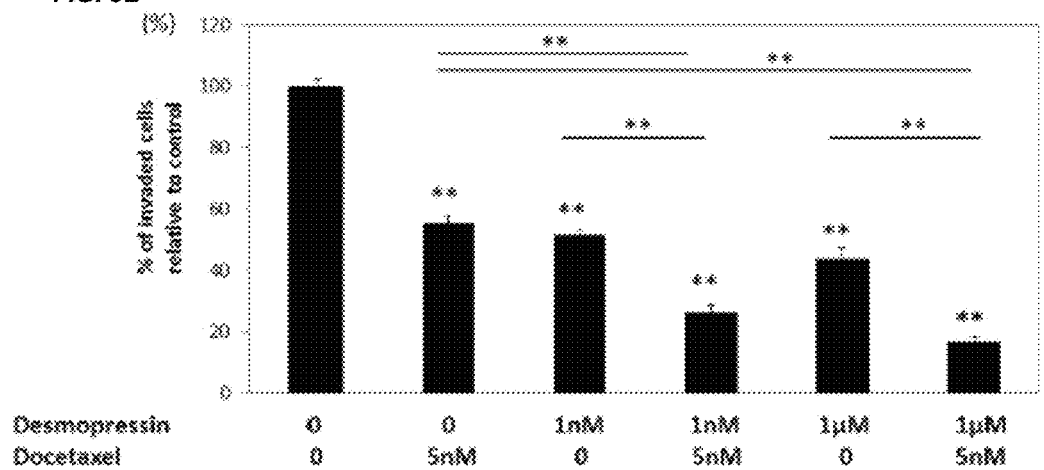
FIG. 3B is a bar graph showing the anti-invasive effects of docetaxel and desmopressin, alone or in combination.

To assess the anti-metastatic ability of desmopressin, a matrigel invasion assay was performed. As shown in FIG. 3, 5 nM docetaxel alone and the two different doses of desmopressin (1 nM and 1 uM) treatment induced significantly inhibition of cell invasion. Furthermore, each combination treatment of 5 nM docetaxel and desmopressin (1 nM and 1 µM) resulted in a significant reduction in cell invasion (FIG. 3, A and B, p<0.01).

Example 4—Effect of Desmopressin in Combination with Docetaxel on Cell Cycle

Desmopressin in combination with docetaxel induces cell cycle arrest and desmopressin enhances the apoptotic effect of docetaxel as determined by western blot analysis.

Figure 4A:
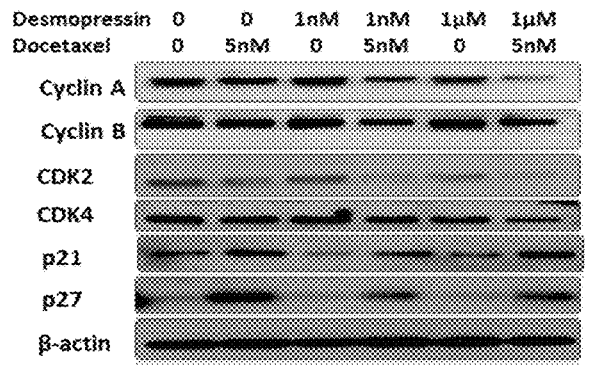
FIG. 4A shows a Western blot analysis on cell proliferation effects of docetaxel and desmopressin, alone or in combination.
Figure 4B:
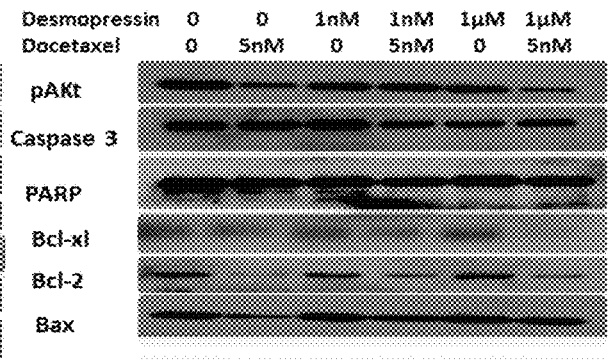
FIG. 4B shows a Western blot analysis on cell apoptosis effects of docetaxel and desmopressin, alone or in combination.
Figure 4C:
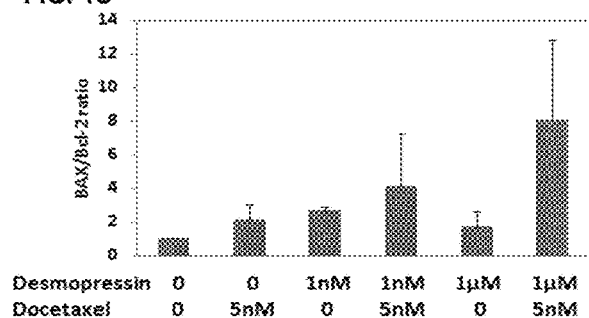
FIG. 4C is a bar graph showing the effects of docetaxel and desmopressin, alone or in combination, on the ratio of Bax/Bcl-2.

To ascertain the results of MTS assay, a western blot analysis was performed to examine cell proliferation. Docetaxel has the ability to alter key regulatory molecules including the suppression of microtubule with consequent mitotic spindle disruption, leading to G2/M phase cell cycle arrest and induction of bcl-2 phosphorylation ultimately leading to apoptosis.[16-18] The expression of cyclin A, cyclin B, CDK2 and CDK4 were reduced in the cells treated with desmopressin and docetaxel (FIG. 4A). In addition the expression of CDK inhibitory protein, p21(waf1/cip1) and p27(kip1) were elevated under the same conditions (FIG. 4A). The results indicate that desmopressin in combination with docetaxel therapy may inhibit the molecules associated with cell cycle progression and concomitantly inducing cell cycle arrest. The ratio of Bax/Bcl-2 revealed a 4 fold and 8 fold increased expression in cells treated with 1 nM desmopressin in combination with docetaxel and 1 µM desmopressin in combination with docetaxel respectively, all expressed relative to control (FIG. 4 C). In addition, both combination treatments reduced expression of total Caspase 3. Desmopressin treatment alone did not reduce the expression of bcl-2, PARP or caspase 3 (FIG. 4, B), which indicates that desmopressin enhances the apoptotic effect of docetaxel.

Example 5—Desmopressin does not Alter Cell Cycle Distribution for Treatment on PC3

Figure 4D:
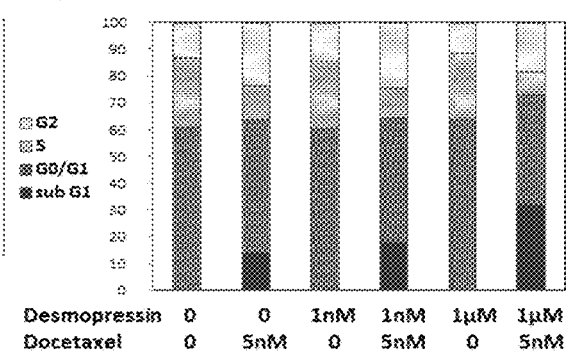
FIG. 4D is a bar graph showing the cell cycle effects of docetaxel and desmopressin, alone or in combination.

Alterations in cell cycle profiles by flow cytometric analysis using BrdU labeling on cells treated with desmopressin and DTX alone and in combination were examined. Treatment with 5 nM docetaxel or a combination with 1 nM/1 µM desmopressin showed a significant increase in the proportion of cells in G2 phase consistent with a G2M cell cycle arrest (FIG. 4D). Furthermore, each combination treatment increased the population of cells in the sub G1 phase indicative of apoptosis.

Figure 5A:
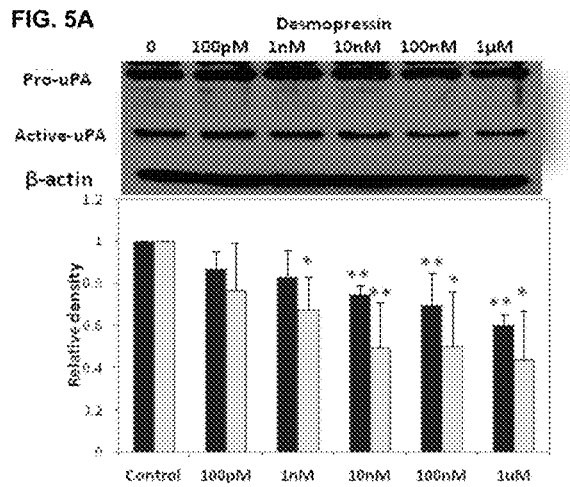
FIGS. 5A-5D are bar graphs showing the effects of desmopressin on expression of pro-uPA, active uPA, MMP-2, MMP-9, and uPAR.
Figure 5B:
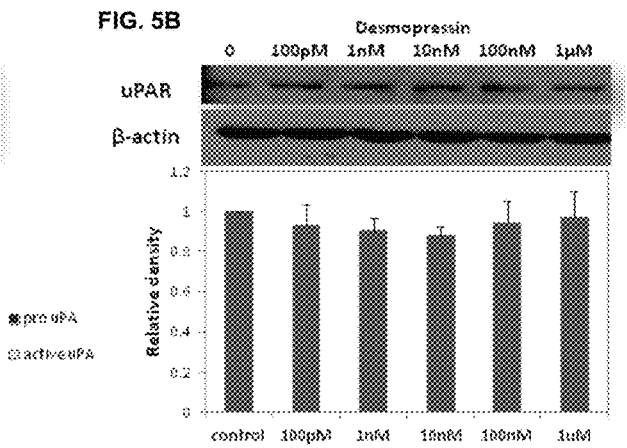
Figure 5C:
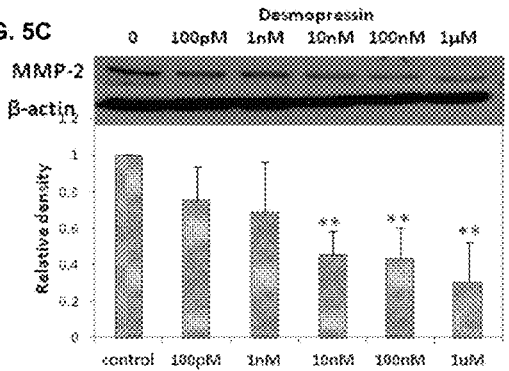
Figure 5D:
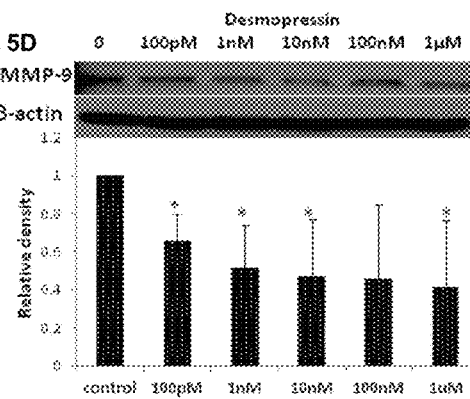
Figure 6A:
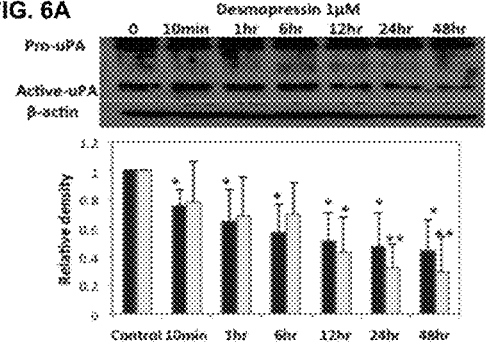
FIGS. 6A-6D are bar graphs showing the effects of desmopressin in a time-dependent manner on the expression of pro-uPA, active uPA, MMP-2, MMP-9, and uPAR.
Figure 6B:
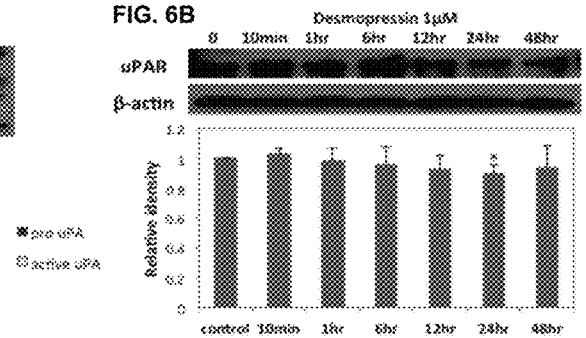
Figure 6C:
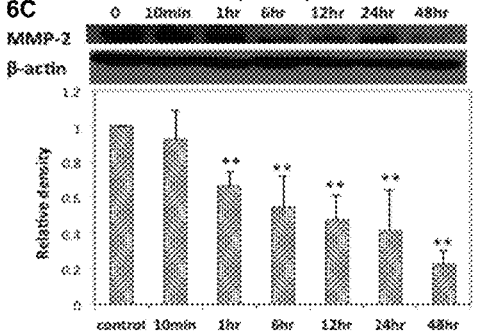
Figure 6D:
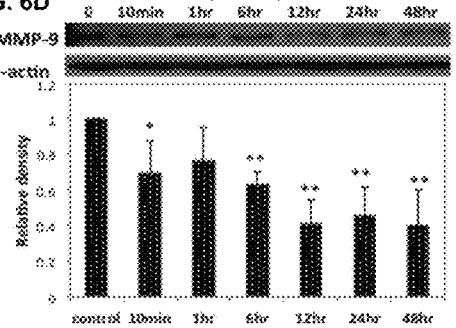
Figure 7:
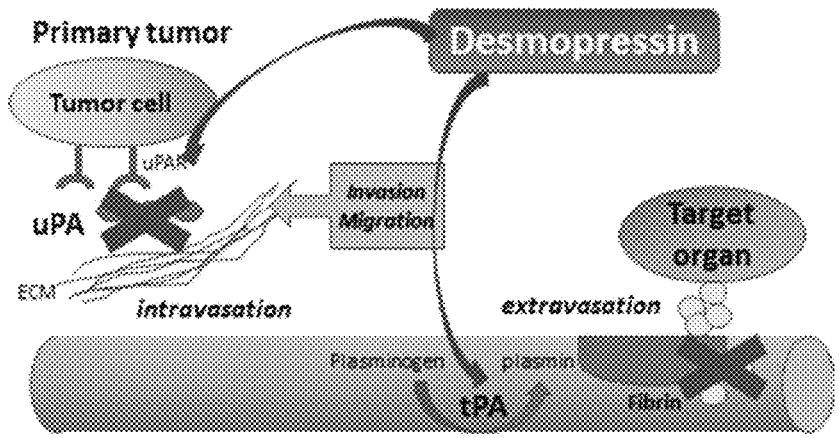
FIG. 7 is a schematic diagram showing, in one embodiment, the effects of desmopressin on tumour cell migration and invasion via the uPA-MMP pathway.

Example 6—Effect of Desmopressin on Migration and Invasion of Prostate Cancer Cells and uPA-MMP Pathway Mediates The two molecules MMPs and uPA are involved in cancer cell invasion, motility and tumor dormancy.[19] Based on the results of migration assay and invasion assay, desmopressin was examined for its anti-metastatic properties in monotherapy. Dose standardization and time point studies were carried out with desmopressin. As shown in FIG. 5, desmopressin monotherapy altered the expression of precursor pro-uPA, active uPA, MMP-2 and MMP-9 all of which were reduced in a dose dependent manner (FIGS. 5A, C and D). In contrast, the expression of uPAR was unaltered (FIG. 5B). In a time point study that was carried out with a concentration of 1 µM desmopressin, the expression of uPA, MMP-2 and MMP-9 was also reduced in a time dependent manner (FIGS. 6A, C and D). However, uPAR expression was not altered (FIG. 6B). Desmopressin monotherapy reduced zymogen type uPA, (also called pro-uPA) expression, thus attenuating uPA activity on the cell surface. These results demonstrate that desmopressin has the ability to inhibit tumor cell migration and invasion via the uPA-MMP pathway (FIG. 7).

Figure 8A:
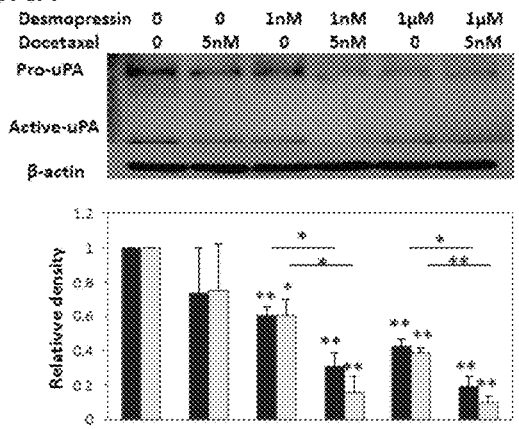
FIGS. 8A-8D are bar graphs showing the effects of docetaxel and desmopressin, alone or in combination, on expression of pro-uPA, active uPA, MMP-2, MMP-9, and uPAR.
Figure 8B:
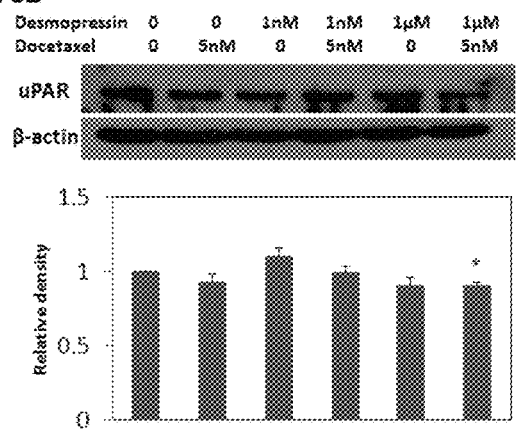
Figure 8C:
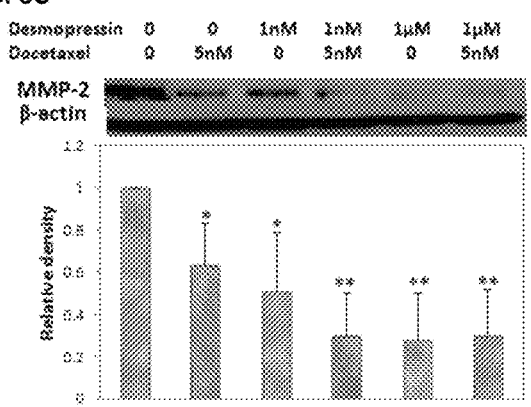
Figure 8D:
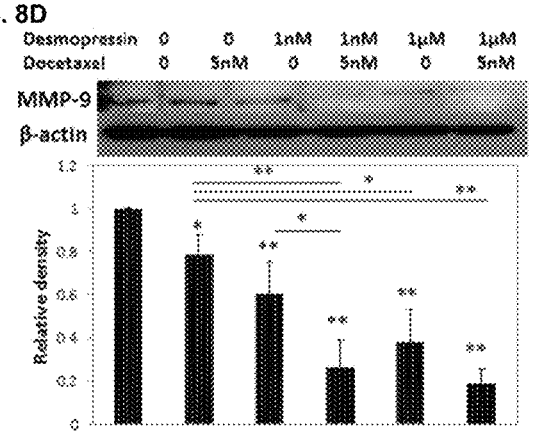

It was also demonstrated that desmopressin in combination with docetaxel inhibited tumor cell migration and invasion. As shown in FIG. 6, combination treatment with 5 nM docetaxel and desmopressin (1 nM and 1 µM) resulted in a reduction in the expression of uPA when compared to control (FIG. 8, A, p<0.01). In addition, the expression MMP-2 was also significantly reduced in the cells treated with each combination therapy compared to control (FIG. 8 C, p<0.01). The expression of uPAR was unaltered, as shown in FIG. 8B. The expression of MMP-9 was significantly reduced in the cells treated with each combination therapy compared to control (FIG. 8, D, P<0.01). Consequently, desmopressin in combination with docetaxel influences the uPA-MMP pathway.

Example 7—Effect of Desmopressin on PC-3 Cell Growth in a Xenograft Model

Figure 9:
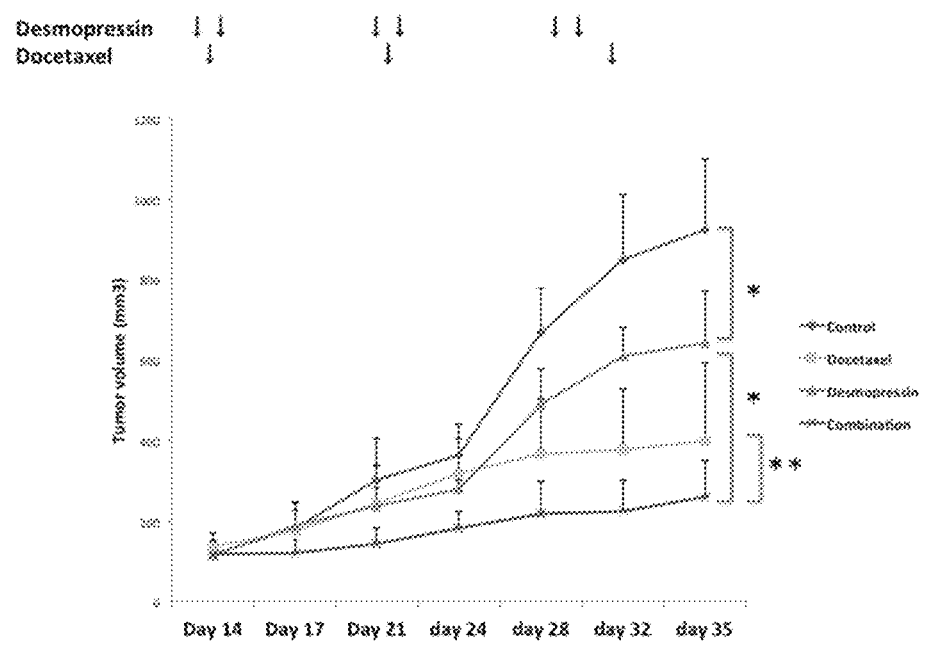
FIG. 9 is a graph showing the effects of docetaxel and desmopressin, alone or in combination, on tumour volume, and also showing the treatment schedule.

The effect of desmopressin alone on tumor growth was examined. As a first step, the inhibition of tumor growth with desmopressin treatment was compared to control animals. Using athymic nude mice, cells were inoculated in matrigel as described above. Tumor volume was assessed twice weekly. Tumors in control animals grew rapidly measuring a volume of 923 mm³ on day 35 post tumor inoculation. On the contrary, tumor growth in the desmopressin treated mice had a significantly slower rate of tumor development reaching a mean volume of 642 mm3 on day 35 (FIG. 9, Student's t-test p<0.01). The tumor volumes between control and desmopressin treatment were significantly different (ANOVA, p<0.0001). Desmopressin was then examined to determine if it was able to enhance the sensitivity of PC3 cells to docetaxel in vivo. As shown FIG. 9, the tumors in the combination group were significantly smaller than either control mice and docetaxel treatment alone (ANOVA, p<0.05). Treatment with intravenous injection of docetaxel and/or desmopressin was well tolerated. All mice consistently maintained their body weight during each study.

DISCUSSION

Components of the fibrinolytic system urokinase plasminogen activator (uPA) and urokinase plasminogen activator receptor (uPAR) facilitate targeted proteolysis of the basement matrix in order for neovascularization to occur. Overexpression of these factors in tumor tissue has been identified as prognostic for metastatic spread and overall survival in many human cancers, including hormone dependent cancers such as gastrointestinal, lung, lung, uterine, endometrial, bladder, ovarian, testicular, breast, colon or prostate cancer. These factors are thought to be directly involved in cancer cell invasion and metastasis. uPA is specifically inhibited by desmopressin.

Desmopressin was found to have anti-proliferative, anti-migration and anti-invasive effects on PC3 cells in vitro and in vivo. Previous reports demonstrated that desmopressin contributes to the reduction of locolegional disease at the time of primary surgery for advanced mammary cancer[11] and inhibited experimental lung colonization when co-injected intravenously with metastatic mammary tumor cells[12]. Ripoll et al. demonstrated that desmopressin had anti-proliferative effects on human colo-205 and mouse CT-26 colon carcinoma cell lines[20]. These studies have focused on cancer cells expressing the V2 receptor. Desmopressin is a selective agonist for the vasopressin V2 receptor[21]. Typically, the V2 receptor is expressed in endothelial cells and the kidney collecting duct, mediating antidiuretic and hemostatic effects. Prostate cancer cell lines do not appear to express the V2 receptor[21-24] The Examples have demonstrated desmopressin anti-tumor and anti-metastatic effects on PC3 cells lacking the V2 receptor.

The above examples have shown that the anti-metastatic activity of desmopressin is mediated through the uPA pathway. Desmopressin monotherapy resulted in a dose-dependent reduction of uPA expression (FIG. 5A). The uPA and its receptor uPAR are expressed in most solid and invasive cancers including PC3 cells. The uPA protein involved in the degradation of the extracellular matrix, facilitating invasiveness and growth[25, 26]. The expression of uPA is upregulated in tumor tissue, making it an attractive therapeutic target for cancer therapy 27, 28. uPA is a member of the serine protease family in strongly implicated as a promotor of tumor progression in various human malignancies including prostate cancer. It is synthesized and secreted as a pro-enzyme. Binding to uPAR, uPA efficiently converts the inactive zymogen, plasminogen, into the active serine protease, plasmin. Plasmin can activate MMPs, potent enzyme that can also digest a variety of extracellular matrix components[29]. The Examples have demonstrated desmopressin as monotherapy and in combination with docetaxel significantly inhibited the expression of uPA, MMP-2 and MMP-9. It did not alter the expression of uPAR. uPA activates MMP-2 and MMP-9 during the migration and invasion of prostate cancer[39-32]. The concept of the key role of the binding of uPA to uPAR derives from several studies demonstrating that the ability of tumor cells to invade and metastasize is downregulated by uPA inhibitors. The results indicate that desmopressin monotherapy reduced pro-uPA expression as well as active uPA, thus attenuating uPA activity on the cell surface. It has been shown that down-regulation of uPA by desmopressin inhibits invasion and migration of prostate cancer cells. Thus, without being bound by theory, desmopressin may be acting to inhibit uPA activity in prostate cancer (FIG. 7).

The growth of prostatic tumor cells related to the activation of the plasminogen activator system is derived from the demonstration that growth rates and uPA production in tumor cells cultured at a low density are higher than those observed in cells grown at higher cell density. This modulation may affect tumor cell proliferation[27]. However, the result of cell proliferation was not consistent with the results of uPA expression in desmopressin monotherapy. Many cytokines and growth factors such as TGFβ1, IGF-1, FGF, EGF and bombesin induce the expression of components of the uPA system[19, 28, 33, 34]. These factors may also be associated with uPA expression and tumor cell proliferation.

Pharmaceutical combinations to reduce dose-limiting toxicity of docetaxel and/or to increase its efficacy are attractive. The Examples have demonstrated that desmopressin monotherapy inhibited cell proliferation (FIG. 1B) and that combination therapy (desmopressin and docetaxel) significantly inhibited cell proliferation in vitro and tumor growth in vivo compared to control (FIG. 1C, FIG. 9). Desmopressin monotherapy did not alter cell cycle distribution and the expression levels of apoptosis related proteins. Nonetheless, it was observed that desmopressin enhanced cell cycle arrest and the apoptotic effect of docetaxel in combination.

Desmopressin influences the secretion of a number of factors including, vWF and tPA. vWF is a multimetric plasma glycoprotein that plays an important role in primary hemostasis, allowing the adhesion of platelets to the exposed subendothelium[35]. Terraube V, et al[36] reported vWF plays protective role against tumor cell dissemination in a vWF deficient mutant mouse model. Restoration of vWF plasma levels by administration of recombinant vWF reduced lung metastasis[35, 36]. Intravenous injection of desmopressin induces the release of vWF, with a time peak levels at about 1 hr[21, 37]. It is thought that vWF might be involved in the interaction of tumor cells with platelets and subendotelium. On the other hand, the main function of t-PA is intravascular fibrinolysis. There is a high affinity that t-PA has for fibrin, reflecting high thrombolytic efficacy, since t-PA is synthesized by vascular endothelial cells and secreted into the blood[38-40]. In addition, tPA may negatively regulate angiogenesis and their inhibitors may promote it[41-46]. Hence, vWF and tPA are important factors influencing the impact of desmopressin on tumor cell invasion and metastasis (FIG. 7).

The Examples have shown that desmopressin monotherapy regulated uPA-MMP expression on PC3 cells at the protein level, not the DNA or RNA levels. Desmopressin alone, or in combination with docetaxel, was shown to reduce tumour volume, inhibit cell proliferation, invasion and migration of prostate cancer cells. Desmopressin has anti-proliferative, anti-migration and anti-invasive effects in prostate cancer.

Example II

In this study, the anti-tumor effect of desmopressin in combination with docetaxel using DU145 cells in vitro and in vivo was investigated.

Materials and Methods

Cell Culture

Castrate resistant prostate cancer cells DU145 was used. Cell culture procedures were followed according to previously described procedures[48, 49].

Chemicals

Docetaxel was purchased from Sigma-Aldrich. Docetaxel was prepared in dimethyl sulfoxide (DMSO; Sigma-Aldrich, MO, USA) and diluted with cell culture medium (0.01% DMSO) for cell culture treatments. Desmopressin was purchased from Ferring© (Octostim 15 μg/mL per ampoule).

Cell Proliferation Assay

Cell proliferation was determined by MTS assay[48,49]. DU145 cells were plated in 96 well plates at a concentration of 4000 cells/well. After 24 hours of attachment, dose standardization was performed, using various concentrations of DTX (1 nM, 10 nM, 100 nM and 1 μM) and Desmopressin (1 nM, 10 nM, 100 nM and 1 μM each). Cell proliferation was assessed using MTS assay at 24, 48 and 72 hours following treatment. Based on the results, cell proliferation assays at similar time points for combination treatments with DTX 10 nM and 100 nM with Desmopressin 1 μM were completed. Results were analysed using two-tailed student t-test with significance level of $p<0.05$ being considered statistically significant.

Wound Healing Assay

The motility inhibitory potential of desmopressin alone and/or in combination with docetaxel was accessed by wound healing assay according to previously described protocol[49,50]. DU145 cell were plated on 24-well plates at a concentration of 50,000 cells per well and were allowed to grow until they reached 90-100% confluence. After incubating the cells with 1 mg/L Mitomycin C (Sigma©) for 1 hour, a vertical scratch across each well was created; floating cells removed and cell media or media with treatment solutions were added. Images were obtained at zero-time point and after 24 hours of treatment. A computer-based microscopy imaging system with ×200 magnification (Axiovision©) was used to measure wound healing of each well. Each experiment was carried out in duplicates and repeated three times In Vivo Studies with Xenograft Model All procedures were done according to the Canadian council on animal care (CCAC) regulations and local animal research ethics board procedures and approval.

6-week old male athymic nude mice (Charles river, QC, Canada) were used to evaluate the effect of combination therapy on DU145 tumor growth in vivo. Mice were housed and maintained in laminar flow cabinets under pathogen-free conditions. Following 2 weeks of housing, $1\times10^6$ DU145 cells per animal in 100 μL matrigel solution (BD Bioscience, CA, USA) were inoculated subcutaneously, according to procedure described by Fridman et al (51). After 14 days following inoculation, body weight and tumor size were measured, and mice were randomly assigned to different treatment groups. Groups included control (sham treatments), DTX (5 mg/kg body weight) intraperitoneally, Desmopressin (2 μg/ml/body weight) intravenously 30 minutes prior to IP injection and 24 hours later or combination therapy (n=4 per group). Each group received treatment once every other week for a total of 3 treatments. Animal weight and tumor measurements were assessed regularly. Tumor size was calculated by length (L) and width (W) measured with caliper according to the following formula: V=(L×W2) (n/6).

Two weeks following the last treatment, mice were euthanized; tumors were excised, measured directly with caliper and sent for histological analysis.

Statistics: Tumor volume calculated during the treatment period were compared using repeated measures one-way ANOVA test (SPSS©). Final tumor volume and body weight measurements were compared separately using one-way ANOVA test.

Results

Cell Proliferation

Figure 10:
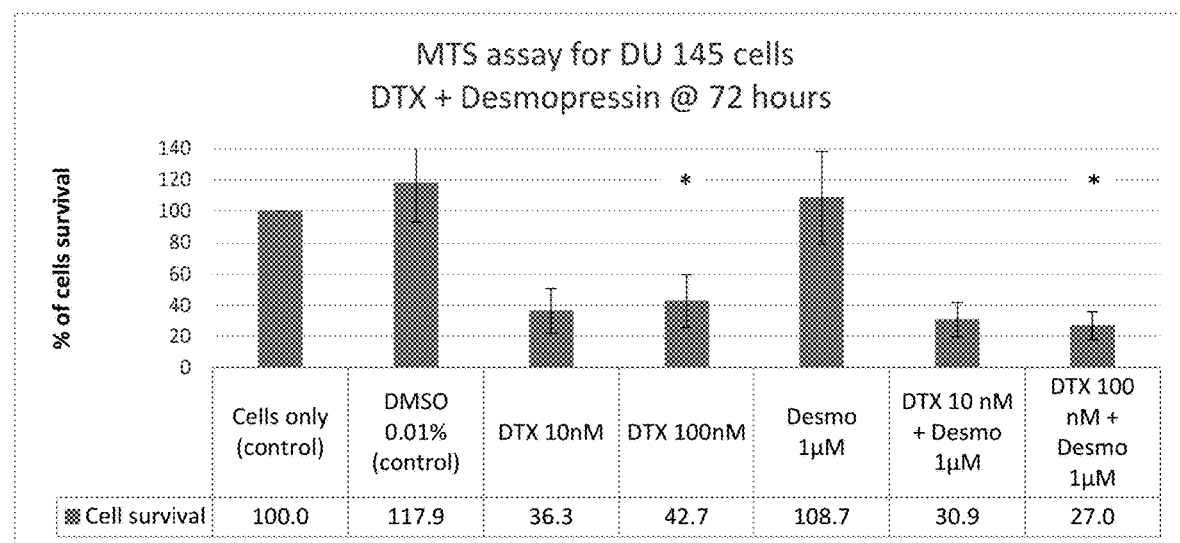
FIG. 10 is a bar graph showing the effects of docetaxel (DTX) or desmopressin (Desmo), alone and/or in combination, on DU145 cells.

After determining optimal concentrations of Desmopressin and docetaxel (Data not shown), a combination therapy of 10 nM and 100 nM of DTX and 1 µM Desmopressin was used. Combined dosages of 100 nM DTX+1 µM Desmopressin resulted in an inhibition of cell proliferation at 72 hours post treatment ($p<0.05$) (FIG. 10). Similar analysis was completed for 24 and 48 hours' time points, and with concentrations of 10 nM DTX, revealing minimal response without statistical significance when compared to DTX treatment alone (Data not shown).

Cell Migration

Figure 11:
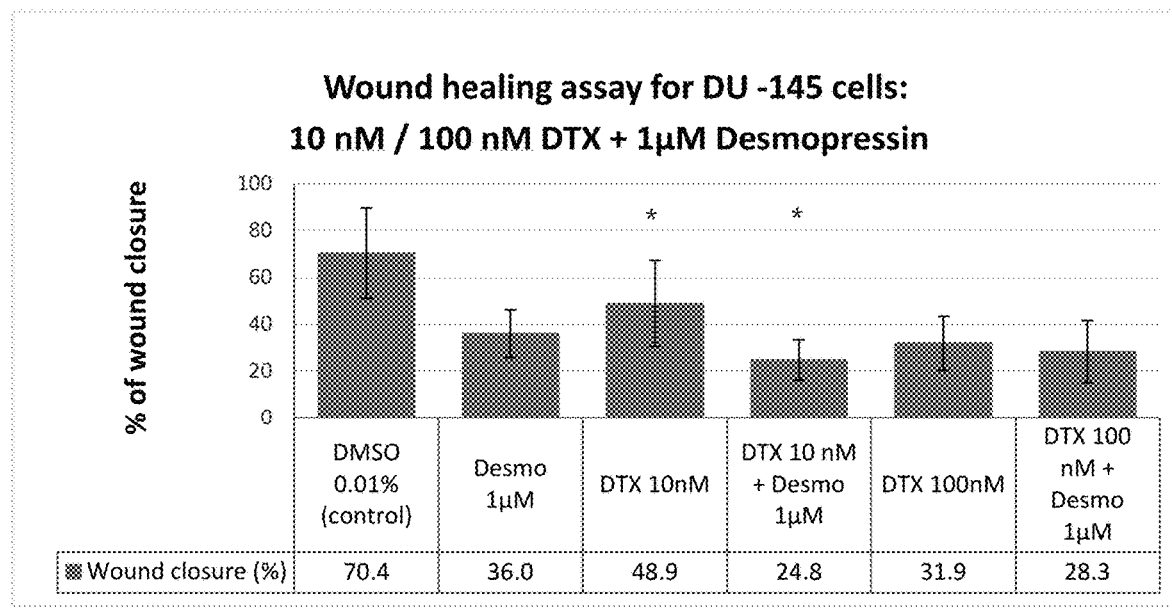
FIG. 11 is a bar graph showing the effects of docetaxel (DTX) or desmopressin (Desmo), alone and/or in combination, on DU145 cells, assessed using wound healing assay.
Figure 12A:
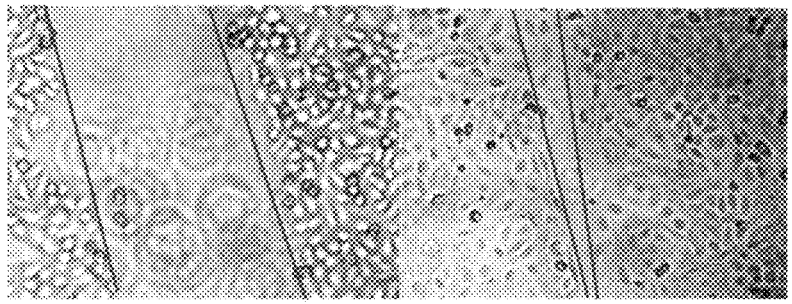
Figure 12B:
Figure 12C:
Figure 12D:
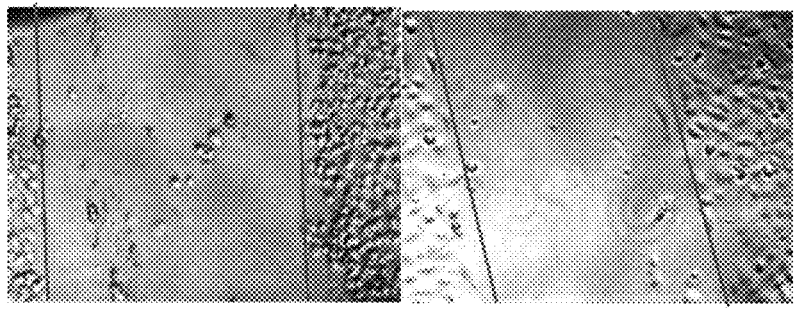

In vitro wound closure was inhibited by combination treatment compared to control and each treatment alone for DTX concentration of 10 nM combined with 1 µM Desmopressin compared to DTX treatment alone (24.8% vs 48.9%, $p<0.05$, two-way student t-test) (FIG. 11). 10 nM DTX alone had migration inhibitory effect when compared to control, while Desmopressin treatment alone had no statistical significant effect. DTX was causing significant cell kill at concentration of 100 µM. Although results for this concentration are shown in FIG. 11, no reliable measurement could be drawn and consequently no result could be observed for those concentrations. Representative pictures of in vitro wound closure are presented in FIG. 12.

In Vivo: Xenograft Mouse Model

Combination therapy (DTX 5 mg/kg I.P and desmopressin 2 µg/ml/body weight IV, 30 minutes before chemotherapy and 24 hours later) resulted in decreased tumor volume (FIG. 13), while not effecting changes in body weight of the animal (FIG. 14). ANOVA analysis revealed significant difference in average tumor sizes for combination therapy starting at day 42 post DU145 inoculation, this being the third therapeutic cycle that was administered to the animals. Representative pictures of the mice bearing tumors and the tumors following excision are shown in FIG. 15.

Final measurement at day on day 55 post inoculation were done directly after tumors were excised, assuming direct measurement would be more precise measurements. Results revealed an average tumor size of 2049±520, 1597±681, 1330±550 and 773±314 mm3 for control, Desmopressin alone, DTX alone and combination therapy respectively. ($P<0.05$ for combination treatment compared to DTX treatment).

DISCUSSION

A combination treatment of DTX and Desmopressin was shown to significantly inhibit prostate cancer cells proliferation and migration. These data showed changes in the proliferative and migratory potential of DU-145 cells as well. In a mouse xenograft model, it was observed that a combination of Desmopressin and DTX significantly reduced tumor growth (as determined by tumor volume) following three treatments of combination therapy compared to treatment using single agents.

REFERENCES CITED HEREIN

1. Jemal A., Siegel R, Ward E, Hao Y, Xu J, Murray T, Thun M J. Cancer statistics, 2008. C A: a cancer journal for clinicianscer journal for clinicians 2008; 58(2):71-96.
2. Hanahan D, Weinberg R A. The Hallmarks of Cancer Review. Cell. 2000; 10057-70.
3. Petrylak D P, Tangen C M, Hussain M H a, et al. Docetaxel and estramustine compared with mitoxantrone and prednisone for advanced refractory prostate cancer. [Internet]. The New England journal of medicine. 2004; 351(15):1513-20.
4. Tannock I F, de Wit R, Berry W R, et al. Docetaxel plus prednisone or mitoxantrone plus prednisone for advanced prostate cancer. [Internet]. The New England journal of medicine. 2004; 351(15):1502-12.
5. Friedland D, Cohen J, Miller R, et al. A phase II trial of docetaxel (Taxotere) in hormone-refractory prostate cancer: correlation of antitumor effect to phosphorylation of Bcl-2. Seminars in oncology. 1999; 26(5):19-23.
6. Berthold D R, Pond G R, Soban F, de Wit R, Eisenberger M, Tannock I F. Docetaxel plus prednisone or mitoxantrone plus prednisone for advanced prostate cancer: updated survival in the TAX 327 study. Journal of clinical oncology: official journal of the American Society of Clinical Oncology. 2008; 26(2):242-5.
7. Picus J, Schultz M. Docetaxel (Taxotere) as monotherapy in the treatment of hormone-refractory prostate cancer: preliminary results. Seminars in oncology. 1999; 26(5 Suppl 17):14-8.
8. Richardson D W, Robinson A G. Desmopressin. Annals of Internal Medicine. 1985; 103228-239.
9. Mannucci P M, Aberg M, Nilsson I M, Robertson B. Mechanism of plasminogen activator and factor VIII increase after vasoactive drugs. British journal of haematology. 1975; 30(1):81-93.
10. Mannucci P M. Desmopressin (DDAVP) in the treatment of bleeding disorders: the first twenty years. Blood. 1997; 902515-2521.
11. Alonso D F, Skilton G, Farias E F, Bal de Kier Joffe E, Gomez D E. Antimetastatic effect of desmopressin in a mouse mammary tumor model. Breast cancer research and treatment. 1999; 57(3):271-5.
12. Giron S, Tejera A M, Ripoll G V, Gomez D E, Alonso D F. Desmopressin inhibits lung and lymph node metastasis in a mouse mammary carcinoma model of surgical manipulation. Journal of surgical oncology. 2002; 81(1): 38-44.
13. Ripoll G V, Giron S, Krzymuski M J, Hermo G a, Gomez D E, Alonso D F. Antitumor effects of desmopressin in combination with chemotherapeutic agents in a mouse model of breast cancer. Anticancer research. 2008; 282607-12.
14. Venkateswaran V, Klotz L H, Fleshner N E. Selenium Modulation of Cell Proliferation and Cell Cycle Biomarkers in Human Prostate Carcinoma Cell Lines Selenium Modulation of Cell Proliferation and Cell Cycle Biomarkers in Human Prostate Carcinoma Cell Lines. Cancer Research. 2002; 62(9):2540-2545.
15. Liang C-C, Park A Y, Guan J-L. In vitro scratch assay: a convenient and inexpensive method for analysis of cell migration in vitro. Nature protocols. 2007; 2(2):329-33.
16. lmmordino M L, Brusa P, Arpicco S, Stella B, Dosio F, Cattel L. P reparation, characterization, cytotoxicity and pharmacokinetics of liposomes containing docetaxel. Journal of Controlled Release. 2003; 91(3):417-429.

17. Mackler N J, Pienta K J. Drug Insight: use of docetaxel in prostate and urothelial cancers. Nature Clinical Practice Urology. 2005; 2(2):92-100.
18. Pienta K J. Preclinical mechanisms of action of docetaxel and docetaxel combinations in prostate cancer. Seminars in Oncology. 2001; 28(4):3-7.
19. Forbes K, Gillette K, Kelley L a, Sehgal I. Increased levels of urokinase plasminogen activator receptor in prostate cancer cells derived from repeated metastasis. World journal of urology. 2004; 22(1):67-71.
20. Ripoll G V, Garona J, Hermo G A, Gomez D E, Alonso D F. Effects of the Synthetic Vasopressin Analog Desmopressin in a Mouse Model of Colon Cancer. Anticancer research. 2010; 30:5049-5054.
21. Kaufmann J E, Vischer U M. Cellular mechanisms of the hemostatic effects of desmopressin (DDAVP). Journal of thrombosis and haemostasis: JTH. 2003; 1(4):682-9.
22. North W G, Fay M J, Du J. MCF-7 breast cancer cells express normal forms of all vasopressin receptors plus an abnormal V2R. Peptides. 1999; 20(7):837-42.
23. North W G. Gene regulation of vasopressin and vasopressin receptors in cancer. Experimental physiology. 2000; 8527S-40S.
24. Zhong M, Boseman M L, Millena A C, Khan S a. Oxytocin induces the migration of prostate cancer cells: involvement of the Gi-coupled signaling pathway. Molecular cancer research: MCR. 2010; 8(8):1164-72.
25. Dano K, Andreasen P A, Grondahl-Hansen J, Kristensen P, Nielsen L S, Skriver L. Plasminogen activators, tissue degradation, and cancer. Advances in cancer research. 1985; 44139-266.
26. Dano K, Grondahl-Hansen J, Eriksen J, et al. The receptor for uPA: stromal cell involvement in extracellular proteolysis during cancer invasion. In: Bond J S and Barrett A J, eds. Proteolysis and Protein Turnover. London: Portland Press. 1993: pp. 239-45.
27. Festuccia C, Dolo V, Guerra F, et al. Plasminogen activator system modulates invasive capacity and proliferation in prostatic tumor cells. Clinical & experimental metastasis. 1998; 16(6):513-28.
28. Hildenbrand R, Allgayer H, Marx A, Stroebel P. Modulators of the urokinase-type plasminogen activation system for cancer. Expert opinion on investigational drugs. 2010; 19(5):641-52.
29. Morgan H, Hill P A. Human breast cancer cell-mediated bone collagen degradation requires plasminogen activation and matrix metalloproteinase activity. Cancer Cell Int 2005; 5:1.
30. Quax P H, de Bart a C, Schalken J a, Verheijen J H. Plasminogen activator and matrix metalloproteinase production and extracellular matrix degradation by rat prostate cancer cells in vitro: correlation with metastatic behavior in vivo. The Prostate. 1997; 32(3):196-204.
31. Festuccia C, Giunciuglio D, Guerra F, et al. Osteoblasts modulate secretion of urokinase-type plasminogen activator (uPA) and matrix metalloproteinase-9 (MMP-9) in human prostate cancer cells promoting migration and matrigel invasion. Oncology research. 1999; 11(1):17-31.
32. Rabbani S A. Metalloproteases and urokinase in angiogenesis and tumor progression. In vivo. 1998; 12(1):135-42.
33. Bologna M, Festuccia C, Muzi P, Biordi L, Ciomei M. Bombesin Stimulates Growth of Human Prostatic Cancer Cells in Vitro. Cancer. 1989; 631714-1720.
34. Jarrard D F, Blitz B F, Smith R C, Patai B L, Rukstalis D B. Effect of epidermal growth factor on prostate cancer cell line PC3 growth and invasion. The Prostate. 1994; 24(1):46-53.
35. Terraube V, Pendu R, Baruch D, et al. Increased metastatic potential of tumor cells in von Willebrand factor-deficient mice. [Internet]. Journal of thrombosis and haemostasis: JTH. 2006; 4(3):519-26.
36. Terraube V, Marx I, Denis C V. Role of von Willebrand factor in tumor metastasis. [Internet]. Thrombosis research. 2007; 120 Suppl S64-70.
37. Mannucci P M: Desmopressin (DDAVP) in the treatment of bleeding disorders, the first 20 years. Blood 90: 2515-2521, 1997.
38. Matuo O, Rijken D C, and Collen D. Thrombosis by human tissue plasminogen activator and urokinase in rabbits with experimental pulmonary embolus. Nature 1981; 291:590-591.
39. Kristensen P, Larsson L I, Nielsen L S, Grondahl Hansen J, Andreasen P A, and Dano K. Human endothelial cells contain one type of plasminogen activator. FEBS Lett 1984; 168:33-37.
40. Husain S S, Gurewich V, and Lipinski B. Purification and partial characterization of a single-chain molecular weight of urokinase from human urine. Arch Biochem Biophys 1983; 220:31-38.
41. Bajou K, Masson V, Gerard R D, et al. The plasminogen activator inhibitor PAI-1 controls in vivo tumor vascularization by interaction with proteases, not vitronectin. Implications for antiangiogenic strategies. The Journal of cell biology. 2001; 152(4):777-84.
42. Bacharach E, Itin A, Keshet E L I. In vivo patterns of expression of urokinase and its inhibitor PAH suggest a concerted role in regulating physiological angiogenesis. Proc. Natl. Acad. Sci. USA. 1992; 89:10686-10690.
43. Chappuis P O, Dieterich B, Sciretta V, et al. Functional evaluation of plasmin formation in primary breast cancer. Journal of clinical oncology: official journal of the American Society of Clinical Oncology. 2001; 19(10):2731-8.
44. Ferrier C M, Suciu S, van Geloof W L, et al. High tPA-expression in primary melanoma of the limb correlates with good prognosis. British journal of cancer. 2000; 83(10):1351-9.
45. Gately S, Twardowski P, Stack M S, et al. The mechanism of cancer-mediated conversion of plasminogen to the angiogenesis inhibitor angiostatin. Proceedings of the National Academy of Sciences of the United States of America. 1997; 94(20):10868-72.
46. Merchan J R, Chan B, Kale S, Schnipper L E, Sukhatme V P. In vitro and in vivo induction of antiangiogenic activity by plasminogen activators and captopril. Journal of the National Cancer Institute. 2003; 95(5):388-99.
47. Ripoll G V, Garona J, Pifano M, Farina H G, Gomez D E, Alonso D F. Reduction of tumor angiogenesis induced by desmopressin in a breast cancer model. Breast Cancer Res Treat. 2013 November; 142(1):9-18.
48. Vanier N. A, Alexandra J. Colquhoun, Hiroshi Sasaki, Alex Kiss, Linda Sugar, Hans Adomat, Neil E. Fleshner, Laurence H. Klotz, Venkateswaran V. Capsaicin: A novel radio-sensitizing agent for prostate cancer. The Prostate. February 2015. 75 (2), 113-125.
49. Sasaki H, Klotz L H, Sugar L M, Kiss A, Venkateswaran V. A combination of desmopressin and docetaxel inhibit cell proliferation and invasion mediated by urokinase-type plasminogen activator (uPA) in human prostate cancer cells. Biochem Biophys Res Commun. 2015 August, 28; 464(3):848-54.

50. Liang cc, Park J L, Guan J L. In vitro screech assay: a convenient and inexpensive method of analysis of cell migration in vitro. Nat Protocol 2. 2007. 329-333.
51. Rafael Fridman, Gabriel Benton, Irina Aranoutova, Hynda K Kleinman, R Daniel Bonfil. Increased initiation and growth of tumor cell lines, cancer stem cells and biopsy material in mice using basement membrane matrix protein (Cultrex or Matrigel) co-injection. Nature protocols. 2012, 7(6): 1138.

The invention claimed is:

1. A method for the treatment of metastatic castrate-resistant prostate cancer consisting of administering to a subject in need thereof, a therapeutically effective amount of desmopressin.

2. The method of claim 1, wherein the subject is a human.

* * * * *